(12) United States Patent
Okano et al.

(10) Patent No.: US 8,889,118 B2
(45) Date of Patent: Nov. 18, 2014

(54) ANTICANCER AGENT CONTAINING DENDRITIC CELL HAVING RNA VIRUS TRANSFERRED THEREINTO

(75) Inventors: Shinji Okano, Fukuoka (JP); Yoshikazu Yonemitsu, Chiba (JP); Katsuo Sueishi, Fukuoka (JP); Satoko Shibata, Fukuoka (JP); Mamoru Hasegawa, Tsukuba (JP); Haruhiko Kondo, Fukuoka (JP)

(73) Assignee: DNA VEC Research Inc., Ibaraki (JP)

( * ) Notice: Subject to any disclaimer, the term of this patent is extended or adjusted under 35 U.S.C. 154(b) by 598 days.

(21) Appl. No.: 11/630,532

(22) PCT Filed: Apr. 28, 2005

(86) PCT No.: PCT/JP2005/008175
§ 371 (c)(1),
(2), (4) Date: Aug. 16, 2007

(87) PCT Pub. No.: WO2006/001122
PCT Pub. Date: Jan. 5, 2006

(65) Prior Publication Data
US 2008/0014183 A1 Jan. 17, 2008

(30) Foreign Application Priority Data

Jun. 24, 2004 (JP) .................................. 2004-187028
Oct. 29, 2004 (WO) .................. PCT/JP2004/016089

(51) Int. Cl.
A61K 48/00 (2006.01)
C12N 15/86 (2006.01)
A61K 38/21 (2006.01)
A61K 38/17 (2006.01)
A61K 35/76 (2006.01)
A61K 39/00 (2006.01)

(52) U.S. Cl.
CPC ............... *A61K 35/76* (2013.01); *A61K 38/215* (2013.01); *A61K 2039/5154* (2013.01); *C12N 2760/18871* (2013.01); *C12N 2760/18832* (2013.01); *A61K 38/179* (2013.01)
USPC ........................................ 424/93.21; 435/456

(58) Field of Classification Search
USPC ........................................ 424/93.21; 435/456
See application file for complete search history.

(56) References Cited

U.S. PATENT DOCUMENTS

| 5,124,148 | A | 6/1992 | Csatary et al. |
| 6,077,519 | A | 6/2000 | Storkus et al. |
| 6,300,090 | B1 | 10/2001 | Steinman et al. |
| 6,472,208 | B1 | 10/2002 | Lemieux et al. |
| 6,479,286 | B1 | 11/2002 | Nelson et al. |
| 6,645,760 | B2 | 11/2003 | Nagai et al. |
| 6,723,532 | B2 | 4/2004 | Nagai et al. |
| 6,734,014 | B1 | 5/2004 | Hwu et al. |
| 6,746,860 | B1 * | 6/2004 | Tokusumi et al. ......... 435/235.1 |
| 7,056,689 | B1 | 6/2006 | Lorence et al. |
| 2002/0002143 | A1 | 1/2002 | Kano et al. |
| 2002/0098576 | A1 | 7/2002 | Nagai et al. |
| 2002/0123479 | A1 * | 9/2002 | Song et al. ..................... 514/44 |
| 2002/0169306 | A1 | 11/2002 | Kitazato et al. |
| 2003/0022376 | A1 | 1/2003 | Kitazato et al. |
| 2003/0166252 | A1 | 9/2003 | Kitazato et al. |
| 2003/0170266 | A1 * | 9/2003 | Kitazato et al. ............. 424/199.1 |
| 2004/0265272 | A1 | 12/2004 | Iwamoto et al. |
| 2005/0013810 | A1 | 1/2005 | Waller et al. |
| 2005/0048030 | A1 * | 3/2005 | Pickles et al. ................. 424/93.2 |
| 2005/0130123 | A1 | 6/2005 | Inoue et al. |
| 2005/0191617 | A1 | 9/2005 | Inoue et al. |
| 2005/0203126 | A1 | 9/2005 | Badorc et al. |
| 2005/0266566 | A1 | 12/2005 | Nagai et al. |
| 2006/0002899 | A1 | 1/2006 | Rice et al. |
| 2006/0104950 | A1 | 5/2006 | Okano et al. |
| 2006/0121003 | A1 | 6/2006 | Gilboa et al. |
| 2007/0009949 | A1 | 1/2007 | Kitazato et al. |
| 2007/0141705 | A1 | 6/2007 | Inoue et al. |
| 2007/0161110 | A1 | 7/2007 | Iida et al. |
| 2007/0248627 | A1 | 10/2007 | Iwadate et al. |
| 2007/0269414 | A1 | 11/2007 | Okano et al. |
| 2008/0031855 | A1 | 2/2008 | Okano et al. |
| 2008/0038234 | A1 | 2/2008 | Hayashi et al. |
| 2008/0199438 | A1 | 8/2008 | Sueishi |
| 2009/0170798 | A1 | 7/2009 | Hara et al. |
| 2009/0246170 | A1 | 10/2009 | Inoue et al. |
| 2010/0184214 | A1 | 7/2010 | Inoue et al. |
| 2010/0266633 | A1 | 10/2010 | Kano et al. |

FOREIGN PATENT DOCUMENTS

| CA | 2571849 A1 | 1/2006 |
| EP | 0 864 645 A1 | 9/1998 |
| EP | 1 186 667 A1 | 3/2002 |
| EP | 1 447 451 | 8/2004 |
| JP | 2000-253876 | 9/2000 |

(Continued)

OTHER PUBLICATIONS

Gowardhan et al. (2003) European Urology Supplements, vol. 2 (6), 38.*
He et al. (2003) J. Biol. Chem., vol. 278(24), 21831-21836.*
Li et al. (2000) J. Virol., vol. 74(14), 6564-6569.*
Gary-Gouy et al. (2002) J. Int. and Cyt. Res., vol. 22, 653-659.*
Adachi et al. (2002), Immunobiol., vol. 206, 354-367.*
Curiel-Lewandrowski et al. (1999), J. Immunol., vol. 163,174-183.*
Dong et al. (2004), EMBO J., vol. 23, 2800-2810.*
Lopez et al. (2003) JID, vol. 187, 1126-1135.*
Ito et al. (1983) Infecton and Immunity, vol. 39(3), 1019-1023.*
Westermann et al., "Retroviral Interleukin-7 Gene Transfer into Human Dendritic Cells Enhances T Cell Activation" *Gene Ther.* 5(2):264-271 (1998).
Kantengwa et al., "Superoxide Anions Induce the Maturation of Human Dendritic Cells," *Am. J. Respir. Crit. Care Med.* 167(3):431-437 (2003).
Akiyama et al., "Enhancement of Antitumor Immunity Against B16 Melanoma Tumor Using Genetically Modified Dendritic Cells to Produce Cytokines," *Gene Ther.* 7(24):2113-2121 (2000).
Alemany et al., "Replicative Adenoviruses for Cancer Therapy," *Nat. Biotechnol.* 18(7):723-727 (2000).
Banchereau and Steinman, "Dendritic Cells and the Control of Immunity," *Nature* 392(6673):245-252 (1998).

(Continued)

*Primary Examiner* — Anne Marie S Wehbe
(74) *Attorney, Agent, or Firm* — Clark & Elbing LLP

(57) ABSTRACT

The present invention provides anticancer agents comprising dendritic cells introduced with RNA viruses. The present invention also provides methods for producing anticancer agents, which comprise the step of preparing dendritic cells introduced with RNA viruses. The present invention also provides methods for treating cancers using dendritic cells introduced with RNA viruses. The present invention provides effective methods for treating cancers, which use RNA viruses and dendritic cells in combination.

18 Claims, 28 Drawing Sheets

(56) References Cited

FOREIGN PATENT DOCUMENTS

| | | |
|---|---|---|
| JP | 2001-503385 A | 3/2001 |
| JP | 2002-272465 | 9/2002 |
| JP | 2005-532286 A | 10/2005 |
| WO | WO 9425627 A1 | 11/1994 |
| WO | WO 97/16539 | 5/1997 |
| WO | WO 98/06437 A2 | 2/1998 |
| WO | WO 00/70055 | 11/2000 |
| WO | WO 00/70070 | 11/2000 |
| WO | WO 03/004616 A2 | 1/2003 |
| WO | WO 03/022215 A2 | 3/2003 |
| WO | WO 03/025570 A1 | 3/2003 |
| WO | WO 03/029475 A1 | 4/2003 |
| WO | WO-03/084956 A1 | 10/2003 |
| WO | WO 03/102183 A1 | 12/2003 |
| WO | WO 2004/020613 | 3/2004 |
| WO | WO 2004/038029 A1 | 5/2004 |
| WO | wo 2005/042737 A | 5/2005 |
| WO | WO-2005/042737 A1 | 5/2005 |

OTHER PUBLICATIONS

Camporeale et al., "Critical Impact of the Kinetics of Dendritic Cells Activation on the in vivo Induction of Tumor-Specific T Lymphocytes," *Cancer Res.* 63(13):3688-3694 (2003).

Cremer et al., "Inhibition of Human Immunodeficiency Virus Transmission to CD4+ T Cells after Gene Transfer of Constitutively Expressed Interferon Beta to Dendritic Cells," *Hum Gene Ther.* 11(12):1695-1703 (2000).

Curiel, "The Development of Conditionally Replicative Adenoviruses for Cancer Therapy," *Clin. Cancer Res.* 6(9):3395-3399 (2000).

Goldszmid et al., "Dendritic Cells Charged with Apoptotic Tumor Cells Induce Long-Lived Protective CD4+ and CD8+ T Cell Immunity Against B16 Melanoma," *J. Immunol.* 171(11):5490-5497 (2003).

He et al., "Inhibition of Tumor Growth with a Vaccine Based on Xenogeneic Homologous Fibroblast Growth Factor Receptor-1 in Mice," *J. Biol. Chem.* 278(24):21831-21836 (2003).

Hiraoka et al., "Enhanced Tumor-Specific Long-Term Immunity of Hemagglutinating Virus of Japan-Mediated Dendritic Cell-Tumor Fused Cell Vaccination by Coadministration with CpG Oligodeoxynucleotides," *J. Immunol.* 173(7):4297-4307 (2004).

Hsu et al., "Vaccination of Patients with B-cell Lymphoma Using Autologous Antigen-Pulsed Dendritic Cells," *Nat. Med.* 2(1):52-58 (1996).

Imboden et al., "The level of MHC Class I Expression on Murine Adenocarcinoma Can Change the Antitumor Effector Mechanism of Immunocytokine Therapy," *Cancer Res.* 61(4):1500-1507 (2001).

Inoue et al., "Further Attenuation of Gene(s)-Deleted Sendai Virus Vectors: Modification of Transcription and Replication Caused Weakened Cytotoxicity," *Mol Ther.* 7(5):S37 (#92) (2003).

Inoue et al., "Nontransmittible Virus-Like Particle Formation by F-Defient Sendai Virus Is Temperature Sensitive and Reduced by Mutations in M and HN Proteins," *J. Virol.* 77(5):3238-3246 (2003).

Jin et al., "Recombinant Sendai Virus Provides a Highly Efficient Gene Transfer into Human Cord Blood-Derived Hematopoietic Stem Cells," *Gene Ther.* 10(3):272-277 (2003).

Jonuleit et al., "Efficient Transduction of Mature CD83+ Dendritic Cells Using Recombinant Adenovirus Suppressed T Cell Stimulatory Capacity," *Gene Ther.* 7(3):249-254 (2000).

Kaneda Y, "Development of HVJ Envelope Vector for Cancer Therapy," *Seikagaku* 75(8):737(#3S51-6) (2003).

Kanyama et al., "Usefulness of Repeated Direct Intratumoral Gene Transfer Using Hemagglutinating Virus of Japan-Liposome Method for Cytosine Deaminase Suicide Gene Therapy," *Cancer Res.* 61(1):14-18 (2001).

Kirn, "Virotherapy for Cancer: Current Status, Hurdles, and Future Directions," *Cancer Gene Ther.* 9(12):959-960 (2002).

Kunisawa and Mayumi, "Application of Novel Drug Delivery System, Fusogenic Liposome, for Cancer Therapy," *Jpn. J. Cancer Chemother. (Gan to Kagaku Ryoho)* 28(5):577-583 (2001).

Le Bon et al., "Cross-Priming of CD8+ T Cells Stimulated by Virus-Induced Type I Interferon," *Nat. Immunol.* 4(10):1009-1015 (2003).

Lundqvist et al., "Nonviral and Viral Gene Transfer into Different Subsets of Human Dendritic Cells Yield Comparable Efficiency of Transfection," *J. Immunotherapy* 25(6):445-454 (2002).

Min et al., "Dendritic Cells Genetically Engineered to Express Fas Ligand Induce Donor-Specific Hyporesponsiveness and Prolong Allograft Survival," *J. Immunol.* 164(1):161-167 (2000).

Mineta et al., "Attenuated Multi-Mutated Herpes Simplex Virus-1 for the Treatment of Malignant Gliomas," *Nat. Med.* 1(9):938-943 (1995).

Mullins et al., "Route of Immunization with Peptide-Pulsed Dendritic Cells Controls the Distribution of Memory and Effector T cells in Lymphoid Tissues and Determines the Pattern of Regional Tumor Control," *J. Exp. Med.* 198(7):1023-1034 (2003).

Nakahara et al., "Dendritic Cells Stimulated with a Bacterial Product, OK-432, Efficiently Induce Cytotoxic T Lymphocytes Specific to Tumor Rejection Peptide," *Cancer Res.* 63(14):4112-4118 (2003).

Nestle et al., "Vaccination of Melanoma Patients with Peptide- or Tumor Lysate-Pulsed Dendritic Cells," *Nat. Med.* 4(3):328-332 (1998).

Okada et al., "Dendritic Cells Transduced with gp100 Gene by RGD Fiber-Mutant Adenovirus Vectors Are Highly Efficacious in Generating Anti-B16BL6 Melanoma Immunity in Mice," *Gene Ther.* 10(22):1891-1902 (2003).

Okano et al., "Recombinant Sendai Virus Vectors for Activated T Lymphocytes," *Gene Ther.* 10(16):1381-1391 (2003).

Sasaki et al., "Efficient and Stable Sendai Virus-Mediated Gene Transfer into Primate Embryonic Stem Cells with Pluripotency Preserved," *Gene Ther.* 12(3):203-210 (2005).

Shibata et al., "Induction of Efficient Antitumor Immunity against Established B16 Melanoma Using Highly Activated Dendritic Cells Produced by Recombinant Sendai Virus Vector" *The 10th Annual Meeting 2004: The Japan Society of Gene Therapy Poster Session* 2:088 (2004).

Steinman, "The Dendritic Cell System and Its Role in Immunogenicity," *Annu. Rev. Immunol.* 9:271-296 (1991).

Steinman, "Dendritic Cells and Immune-Based Therapies," *Exp Hematol.* 24(8):859-862 (1996).

Steitz et al., "Depletion of CD25(+) CD4(+) T cells and Treatment with Tyrosinase-Related Protein 2-Transduced Dendritic Cells Enhance the Interferon Alpha-Induced, CD8(+) T-Cell-Dependent Immune Defense of B16 Melanoma," *Cancer Res.* 61(24):8643-8646 (2001).

Strome et al., "Strategies for Antigen Loading of Dendritic Cells to Enhance the Antitumor Immune Response," *Cancer Res.* 62(6):1884-1889 (2002).

Sumimoto et al., "Rapid and Efficient Generation of Lentivirally Gene-Modified Dendritic Cells from DC Progenitors with Bone Marrow Stromal Cells," *J. Immunol. Methods* 271(1-2):153-165 (2002).

Teitz-Tennenbaum et al., "Radiotherapy Potentiates the Therapeutic Efficacy of Intratumoral Dendritic Cell Administration," *Cancer Res.* 63(23):8466-8475 (2003).

Xia et al., "Lymphotactin Cotransfection Enhances the Therapeutic Efficacy of Dendritic Cells Genetically Modified with Melanoma Antigen gp100," *Gene Ther.* 9(9):592-601 (2002).

International Search Report from PCT/JP2005/008175 mailed Aug. 18, 2005.

Li et al., "A Cytoplasmic RNA Vector Derived from Nontransmissible Sendai Virus with Efficient Gene Transfer and Expression," *J. Virol.* 74(14):6564-6569 (2000).

Goldszmid et al., "Dendritic Cells Charged with Apoptotic Tumor Cells Induce Long-Lived Protective CD4+ and CD8+ T Cell Immunity Against B16 Melanoma," *J. Immunol.* 171(11):5940-5947 (2003).

Aboagye-Mathiesen et al "Production Interferons in Human Placental Trophoblast Subpopulations and Their Possible Roles in Pregnancy," *Clinical and Diagnostic Laboratory Immunology*, vol. 1:6:650-659 (1994).

Okada et al., "Cytolysis of Sendai virus-infected guinea-pig cells by homologous complement," *Immunologyl*, 49:29:29-35 (1983).

Opolski et al., "Sendai Virus Infection of Tumor Cells Increases the Production of Autoreactive H-2 Specific Antibodies in Syngeneic

(56) References Cited

OTHER PUBLICATIONS

Recipients," *MHC+X: Complex Formation and Antibody induction: Proceedings of the Workshop—Symposium meeting* 66-71 (1988).
Udayakumar et al., "Pharmacological Inhibition of FGF Receptor Signaling Inhibits LNCaP Prostate Tumor Growth, Promatrilysin, and PSA Expression," *Molecular Carcinogenesis* vol. 38:70-77 (2003).
Wakamiya et al., "Tumor Cells Treated with *Vaccinia virus* Can Activate the Alternative Pathway of Mouse Complement," *Jpn. J. Cancer Res.* 80:765-770 (1989).
Supplemental European Search Report (EP 05736740) mailed Oct. 9, 2007.
Supplemental European Search Report (EP 05737340) mailed Oct. 16, 2007.
Engelmayer et al., "*Vaccinia virus* Inhibits the Maturation of Human Dendritic Cells: A Novel Mechanism of Immune Evasion," *J. Immunol.* 163(12):6762-6768 (1999).
Printout of Horst Ibelgaufts' COPE: Cytokines & Cells Online Pathfinder Encyclopaedia (http://www.copewithcytokines.de/cope.cgi?key=NPIC), Jul. 24, 2007, revised Jun. 14, 2010.
Li et al., "Epstein-Barr Virus Inhibits the Development of Dendritic Cells by Promoting Apoptosis of their Monocyte Precursors in the Presence of Granulocyte Macrophage-Colony-Stimulating Factor and Interleukin-4," *Blood.* 99(10):3725-3734 (2002).
Naik et al., "Development of Murine Plasmacytoid Dendritic Cell Subsets," *Immunol. Cell Biol.* 83(5):563-570 (2005).
Salio et al., "Inhibition of Dendritic Cell Maturation by Herpes Simplex Virus," *Eur. J. Immunol.* 29(10):3245-3253 (1999).
U.S. Appl. No. 11/922,278, filed Dec. 13, 2007, Yasuji Ueda et al., Title of Invention: Methods for Producing Antibodies.
Gasperi et al., "Retroviral Gene Transfer, Rapid Selection, and Maintenance of the Immature Phenotype in Mouse Dendritic Cells," *J. Leukoc. Biol.* 66(2):263-267 (1999).
Sato, "Human Dendritic Cells," *Biotherapy* 18(6):467-477 (2004).
Abidi et al., "Cell-Mediated Cytotoxicity Against Targets Bearing Sendai Virus Glycoproteins in the Absence of Viral Infection," *J. Virol.* 50(2):380-386 (1984).
Gary-Gouy et al., "Type I Interferon Production by Plasmacytoid Dendritic Cells and Monocytes Is Triggered by Viruses, but the Level of Production Is Controlled by Distinct Cytokines," *J. Interferon Cytokine Res.* 22(6):653-659 (2002).
Journal of Dalian Medical College 7(3):73-78 (1985).
English Language Translation of Journal of Dalian Medical College 7(3): p. 75, lines 16-24 (1985); in Corresponding Chinese Application Serial No. CN200580028403.6.
Siegel et al., "The Nature of the Principal Type 1 Interferon-Producing Cells in Human Blood," *Science* 284(5421):1835-1837 (1999).
Wheelock, "The Effects of Nontumor Viruses on Virus-Induced Leukemia in Mice: Reciprocal Interference Between Sendai Virus and Friend Leukemia Virus in DBA/2 Mice," *Proc. Natl. Acad. Sci. USA* 55(4):774-780 (1966).
Xu et al., "Biological Feature and Antitumor Role of Endostatin," *China J. Cancer Prev. Treat.* 10(4):423-426 (2003).

Yang et al., The Co-Expression of TNF-α, IFN-β Gene Controlled by HLA-B7 Promoter Enhances Antitumor Effect, *Chin. J. Microbiol. Immunol.* 23(4):275-278 (2003).
Office Action for U.S. Appl. No. 10/578,085, issued Nov. 5, 2009.
López et al., "Type I Interferon Induction Pathway, but Not Released Interferon, Participates in the Maturation of Dendritic Cells Induced by Negative-Strand RNA Viruses," *J. Infect. Dis.* 187(7):1126-1136, 2003.
Lin et al., "Macrophage-Tropic HIV Induces and Exploits Dendritic Cell Chemotaxis," *J. Exp. Med.* 192(4):587-593 (2000).
Visintin et al., "Regulation of Toll-Like Receptors in Human Monocytes and Dendritic Cells," *J. Immunol.* 166:249-255 (2001).
"Dendritic Cell Maturation," published in *R&D Systems Minireviews* on Jan. 1, 2002. Retrieved online Oct. 25, 2011 from http://rndsystems.com/mini_review_detail_objectname_MR02_DendriticCellMat.aspx.
Yoneyama et al., "Development of Immunostimulatory Virotherapy Using Non-Transmissible Sendai Virus-Activated Dendritic Cells," *Biochem. Biophys. Res. Commun.* 355(1):129-135 (2007).
Office Action issued in U.S. Appl. No. 10/578,085 on Jul. 29, 2011.
Hidaka et al., "Nucleotide Sequence of a Sendai Virus Genome Region Covering the Entire M Gene and the 3' Proximal 1013 Nucleotides of the F Gene," *Nucleic Acids Res.* 12(21):7965-7973 (1984).
Shioda et al., "Sequence of 3,687 Nucleotides from the 3' End of Sendai Virus Genome RNA and the Predicted Amino Acid Sequences of Viral NP, P and C Proteins," *Nucleic Acids Res.* 11(21):7317-7330 (1983).
Shioda et al., "Determination of the Complete Nucleotide Sequence of the Sendai Virus Genome RNA and the Predicted Amino Acid Sequences of the F, HN and L Proteins," *Nucleic Acids Res.* 14(4):1545-1563 (1986).
Kato et al., "Initiation of Sendai Virus Multiplication from Transfected cDNA or RNA with Negative or Positive Sense," *Genes Cells* 1:569-579, 1996.
Chen et al., "The Phenotypes and Immune Stimulating Activity of Interleukin-18 Gene-Modified Dendritic Cells," *Chin. J. Cancer Biother.* 6(2):111-116, 1999.
English Translation of Chen et al., "The Phenotypes and Immune Stimulating Activity of Interleukin-18 Gene-Modified Dendritic Cells," *Chin. J. Cancer Biother.* 6(2):111-116, 1999; in a corresponding Chinese application (CN 200480039819.3).
Romani et al., "Proliferating Dendritic Cell Progenitors in Human Blood," *J. Exp. Med.* 180:83-93, 1994.
Okano et al., "Provision of Continuous Maturation Signaling to Dendritic Cells by RIG-I-Stimulating Cytosolic RNA Synthesis of Sendai Virus," J. Immunol. 186(3):1828-1839 (2011).
Romani et al., "Proliferating Dendritic Cell Progenitors in Human Blood," *J. Exp. Med.* 180:83-93 (1994).
Office Action for U.S. Appl. No. 10/578,085, dated Mar. 27, 2012 (24 pages).
Ito et al., "A CD1a+/CD11c+ subset of human blood dendritic cells is a direct precursor of Langerhans cells," J Immunol 163:1409-1419 (1999).

* cited by examiner

FIG. 22

SEQUENCE LISTING

<160> NUMBER OF SEQ ID NOS: 3

<210> SEQ ID NO 1
<211> LENGTH: 10
<212> TYPE: PRT
<213> ORGANISM: Artificial
<220> FEATURE:
<223> OTHER INFORMATION: an artificially synthesized peptide

<400> SEQUENCE: 1

Glu Ala Ala Gly Ile Gly Ile Leu Thr Val
1               5                   10

```
<210> SEQ ID NO 2
<211> LENGTH: 10
<212> TYPE: PRT
<213> ORGANISM: Artificial
<220> FEATURE:
<223> OTHER INFORMATION: an artificially synthesized peptide

<400> SEQUENCE: 2

Glu Leu Ala Gly Ile Gly Ile Leu Thr Val
1               5                   10

<210> SEQ ID NO 3
<211> LENGTH: 9
<212> TYPE: PRT
<213> ORGANISM: Artificial
<220> FEATURE:
<223> OTHER INFORMATION: an artificially synthesized peptide

<400> SEQUENCE: 3

Gly Ile Leu Gly Phe Val Phe Thr Leu
1               5
```

ANTICANCER AGENT CONTAINING DENDRITIC CELL HAVING RNA VIRUS TRANSFERRED THEREINTO

CROSS-REFERENCE TO RELATED APPLICATIONS

This application is the U.S. National Stage of International Application No. PCT/JP2005/008175, filed Apr. 28, 2005, which claims the benefit of Japanese Patent Application No. 2004-187028, filed Jun. 24, 2004, and International Application No. PCT/JP2004/016089, filed Oct. 29, 2004.

TECHNICAL FIELD

The present invention relates to the field of cancer therapy.

BACKGROUND ART

Replicative virus-based therapies (virotherapy) for advanced cancer have been clinically studied in recent years. Virotherapy is a therapeutic strategy in which tumor cells are infected with a replicative virus, such as HSV-1 and adenoviruses, to cure tumors by the cell-killing effect of the is associated with the virus propagation When HSV-1 or an adenoviras is used as the replicative virus for antitumor therapy, the virus is a mutant whose viral genome has been altered by genetic manipulation, such that it retains the ability to replicate in tumors while its pathogenicity to normal human tissues has been minimized. The therapeutic replicative viruses that infect tumor cells replicate in the cells, and infected cells are killed during this process. The propagated viruses again infect nearby tumor cells and thus the antitumor effect spreads (Alemany R. et al., Replicative adenoviruses for cancer therapy. Nat Biotechnol., 2000, 18:723-727; Curiel, D. T., The development of conditionally replicative adenoviruses for cancer therapy, Clin Cancer Res., 2000, 6:3395-9; Kim, D., Virotherapy for cancer: Current status, hurdles, and future directions, Cancer Gene Therapy, 9:959-960, 2002; Mineta T. et al., Attenuated multi-mutated herpes simplex virus-1 for the treatment of malignant gliomas. Nat Med 1:938-943, 1995). Anticancer virotherapy can be used in combination with convention therapeutic methods, such as surgery, radiation therapy, and chemotherapy, and is practically superior because of its wide applicability: it is generally applicable to solid cancers; the virus can be repeatedly administered; and the antitumor effect can be potentiated by directly inserting therapeutic genes, such as those encoding cytokines, into the viral genome; and so on. The development of more effective virotherapy is expected to significantly contribute to anticancer treatment.

Non-Patent Document 1: Alemany R. et al., Replicative adenoviruses for cancer therapy. Nat Biotechnol., 2000, 18:723-727

Non-Patent Document 2: Curiel, D. T., The development of conditionally replicative adenovirwes for cancer therapy, Clin Cancer Res, 2000, 6:3395-9

Non-Patent Document 3: Kim, D, Virotherapy for cancer: Current status, hurdles, and fixture directions, Cancer Gene Therapy, 2002, 9:959-960

Non-Patent Document 4: Mineta T. et al., Attenuated multi-mutated herpes simplex virus-1 for the treatment of malignant gliomas. Nat Med, 1995, 1:938-943

DISCLOSURE OF THE INVENTION

Problems to be Solved by the Invention

The present invention provides anticancer agents comprising dendritic cells introduced with RNA viruses. The present invention also provides methods for producing anticancer agents, which comprise the step of preparing dendric cells introduced with RNA viruses. The present invention also provides methods for treating cancer using dendritic cells introduced with RNA viruses.

Means to Solve the Problems

The present inventors discovered that introducing dendritic cells with an RNA virus able to replicate its genome activated the dendritic cells, producing superior anticancer effects. The cancer growth-suppressing effect produced upon delivering an RNA virus to a cancer via dendritic cells was significantly stronger than that produced when the RNA virus was injected directly into the cancer. Since RNA vises can be introduced into dendritic cells ex vivo, the conditions of viral introduction can be strictly controlled compared to in conventional virotherapy, and greater safety can be achieved by removing viruses that have not infected the dendritic cells. Even dendritic cells introduced with a defective RNA virus that did not release infectious virus were found to produce the same anticancer effects. Specifically, replication of the genomic RNA of an RNA virus in dendritic cells introduced with that RNA virus is essential for their anticancer effect; however, there is no need for the infection to spread to nearby cells via the release of infectious virions. Thus, virotherapy can be carried out using very safe RNA viruses in which the ability to form infectious virions has been eliminated, for example, by deleting viral genes encoding proteins essential for the formation of infectious virions, such as viral envelope proteins.

Specifically, the present invention relates to anticancer agents comprising dendritic cell introduced with RNA viruses, methods for producing the anticancer agents, and methods for suppressing cancers using dendritic cells introduced with RNA viruses. More specifically, the present invention relates to each of the inventions set forth in the claims. Inventions comprising a combination of one or more inventions set forth in claims citing the same claim(s are also intended by the inventions set forth in these claims. Specifically, the present invention relates to:

[1] an anticancer agent which comprises a dendritic cell introduced with an RNA virus able to replicate its genome;

[2] the anticancer agent of [1], wherein the RNA virus does not encode a foreign protein,

[3] the anticancer agent of [1] or [2], wherein the RNA virus is a replication-defective virus the does not form an infectious virion;

[4] the anticancer agent of [1] or [3], wherein the RNA virus encodes a soluble FGF receptor of an IFN-β;

[5] the anticancer agent of any of [1] to [4], wherein the RNA virus is an infectious or non-infectious virion;

[6] the anticancer agent of any of [1] to [4], wherein the RNA virus is a genome RNA-protein complex;

[7] a method for producing an anticancer agent, which comprises the step of introducing a dendritic cell with an RNA virus able to replicate its genome; and

[8] a method for suppressing a cancer, which comprises the step of administering a dendritic cell introduced with an RNA virus able to replicate its genome.

BRIEF DESCRIPTION OF THE DRAWINGS

FIG. 22 depicts a graph showing the growth induction of antigen-specific T cells by dendritic cells introduced with an RNA virus.

BEST MODE FOR CARRYING OUT THE INVENTION

Figure 1:
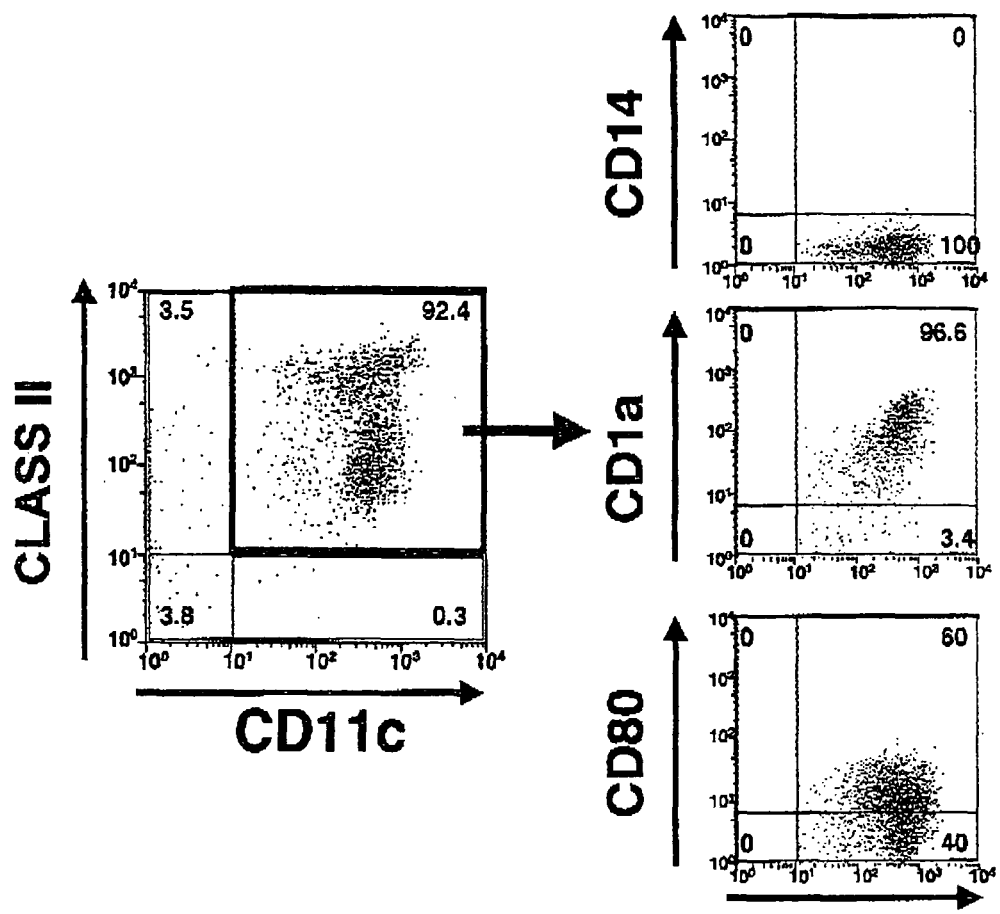
FIG. 1 depicts graphs showing phenotypes of dendritic cells derived from mononuclear cells in monocyte-enriched peripheral blood cells. Viable cells recognized by PI were gated, and the expression of CD11c and HLA-class II (DR, DP, and DQ) was observed using anti-CD11c-PE-conjugated antibody and anti-HLA-class II (DR, DP, and DQ) FITC-conjugated antibody (the left matrix). Furthermore, a gate was selected for both cells positive for both CD11c and HLA-class II (DR, DP, and DQ), and expression levels were detected with: (1) anti-CD14-APC-conjugated antibody; (2) anti-CD1a-APC-conjugated antibody; and (3) anti-CD80-biotin-conjugated antibody (secondarily stained with steptavidin-APC) relative to that of CD11c are shown in dot plots (the tree matrices on the right). In the Examples, "Class II" indicates a result obtained using an antibody recognizing all of HLA-DR, DQ, and DP, and "HLA-DR" indicates a result obtained using an antibody specifically recognizing HLA-DR.
Figure 2:
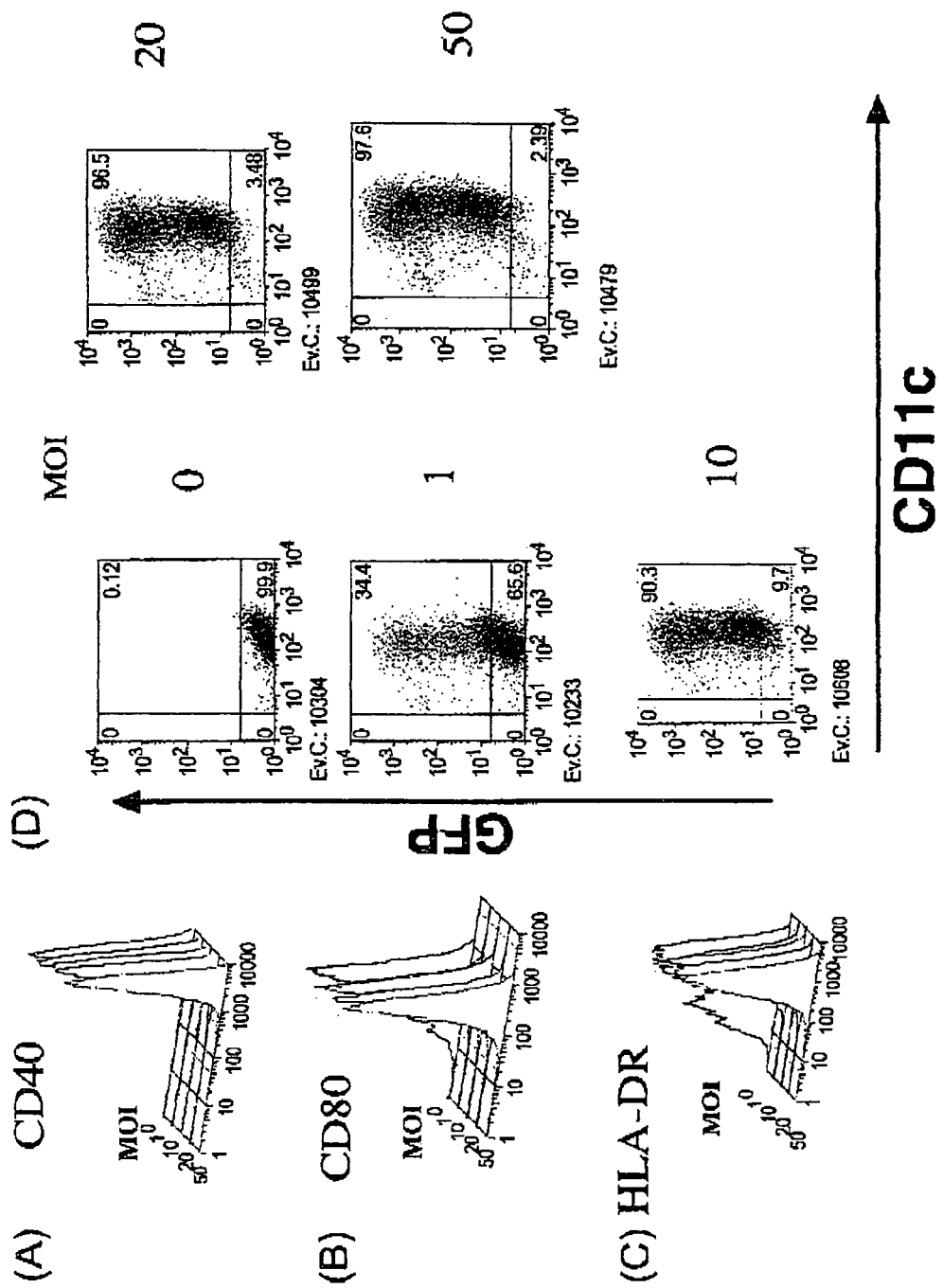
FIG. 2 depicts graphs showing the expression of GFP and costimulatory molecules in DCs introduced with a GFP-expressing RNA virus.
Figure 3:
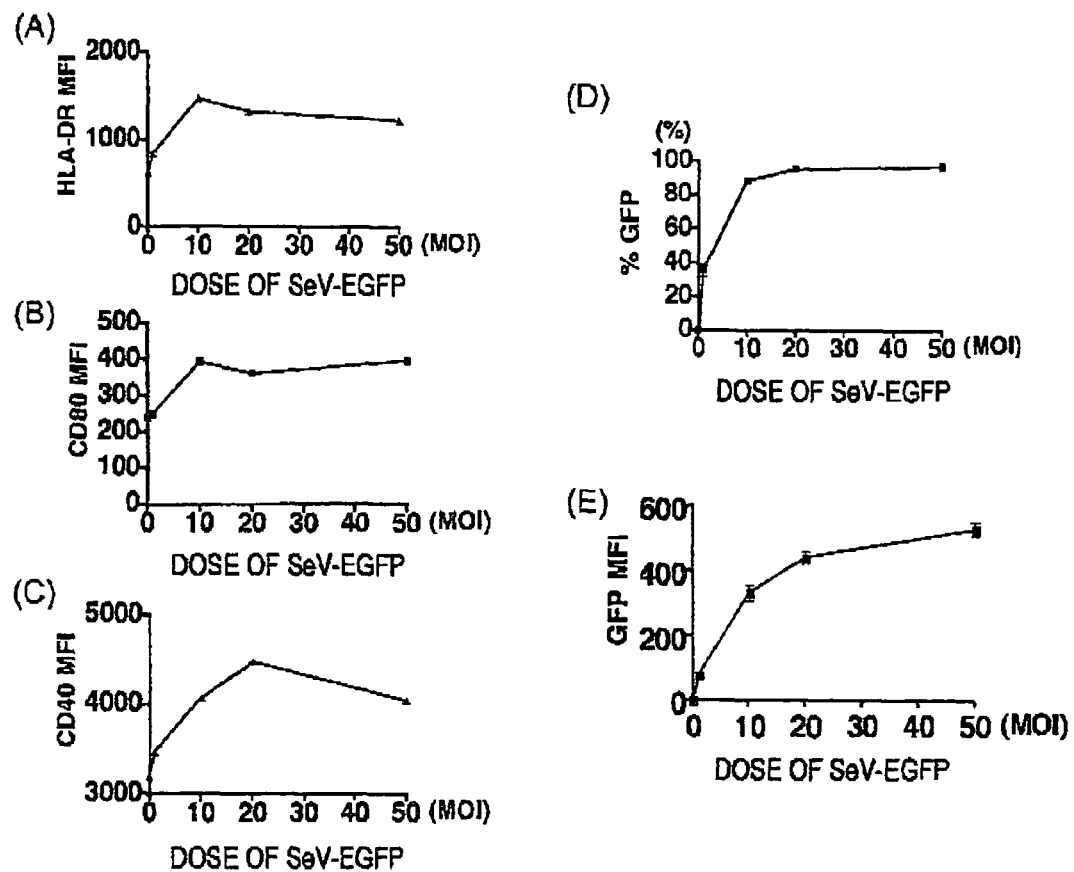
FIG. 3 depicts graphs showing the introduction efficiency of a GFP-expressing RNA virus into human monocyte-derived dendritic cells and the activation of the dendritic cells (day after infection).
Figure 4:
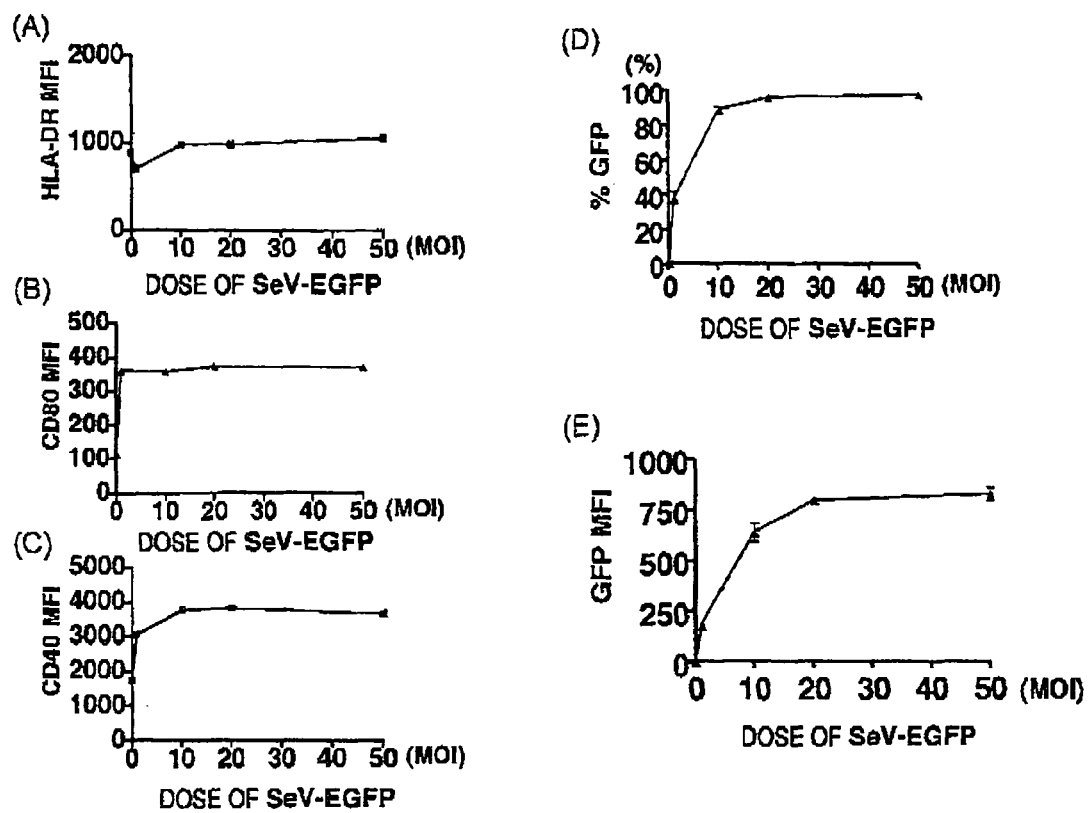
FIG. 4 depicts graphs showing the introduction efficiency of a GFP-expressing RNA virus into human monocyte-derived dendritic cells and the activation of the dendritic cells (day after infection).
Figure 5:
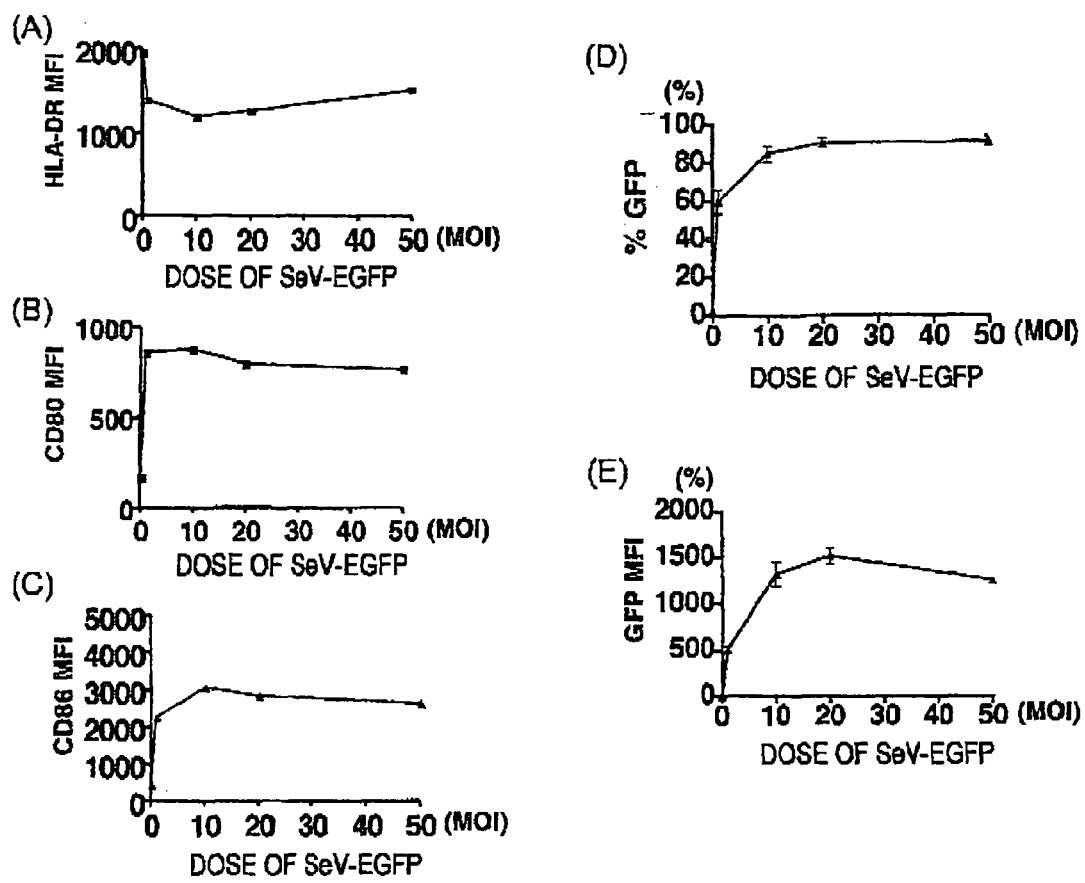
FIG. 5 depicts graphs showing the introduction efficiency of a GFP-expressing RNA virus into human monocyte-derived dendritic cells and the activation of the dendritic cells (day after infection).

The present invention provides anticancer agents comprising dendritic cells introduced with RNA viruses able to replicate their genome. In the present invention, an RNA virus refers to a virus with an RNA genome. Preferably, the RNA viruses of the present invention are viruses whose RNA is synthesized in the viral life cycle by using RNA as a template. The RNA viruses may be desired RNA viruses that replicate their genomic RNAs in dendritic cells, and they may be wild type viruses, or mutant viruses such as attenuated viruses or temperature-sensitive viruses. Alternatively, the RNA viruses may be natural viruses (naturally occurring viruses) or recombinant vie. The RNA viruses include single-stranded RNA viruses (comprising plus strand RNA viruses and minus strand RNA viruses) and double-stranded RNA viruses. The RNA viruses include viruses with envelopes (enveloped viruses) and viruses with no envelope (non-enveloped viruses). The enveloped viruses are preferably used. Specifically, the RNA viruses of the present invention include viruses belonging to the following viral families:

Arenaviridae, including Lassa virus;
Orthomyxoviridae, including influenza virus.
Coronaviridae, including SARS virus;
Togaviridae, including rubella virus;
Paramyxoviridae, including mumps virus, measles virus, Sendai virus, and RS virus;
Picornaviridae, including poliovirus, Coxsackie virus, and echovirus;
Filoviridae, including Marburg virus and Ebola virus;
Flaviviridae, including yellow fever virus, dengue fever virus, hepatitis C virus, and hepatitis G virus;
Bunyaviridae;
Rhabdoviridae, including rabies virus; and
Reovirdae.

In the present invention, "dendritic cells introduced with RNA viruses able to replicate their genome" refers to dendritic cells carrying the genomic RNA of an RNA virus able to replicate its genome, where the RNA is replicated in the cells by the viral proteins encoded by that RNA. The genomic RNAs of the RNA viruses and the viral proteins that bind to the RNA form ribonucleoprotein (RNP) complexes in the cells, and thus the genomic RNAs are replicate in the cells. These RNPs are also called "nucleocapsids". Specifically, in the present invention, "dendritic cells introduced with RNA viruses able to replicate their genome" refers to dendritic cells carrying the ribonucleoproteins (nucleocapsids) of RNA viruses able to replicate their genome.

Dendritic cells introduced with RNA viruses can be obtained by infecting dendritic cell or precursor cells thereof with an RNA virus by contact with infectious RNA virions. Alternatively, without using infectious virions, the cells may be introduced with an RNP of an RNA virus able to replicate its genome, or the cells may be introduced with non-infectious virions comprising the RNP (called non-infectious virions or virus-like particles (VLPs)). Ever RNPs (viral cores) yielded by removing the envelope or coat from virions can also replicate the viral genomic RNA in dendritic cells when introduced into the cells (WO 97/16538; WO 00/70055). Alternatively, expression vectors encoding the viral genomic RNAs and viral proteins (N, P, and L proteins in minus strand RNA viruses) required for the replication of genomic RNAs may be introduced into dendritic cells to form RNPs in the cells. Known transfection methods can be used to introduce RNPs or VLPs into dendritic cells or precursor cells thereof. Specifically, such transfection of dendritic cells can be achieved by various techniques known to those skilled in the art, such as using calcium phosphate (Chen, C. & Okayama, H. (1988) BioTechniques 6:632-638; Chen, C. and Okayama, H., 1987, Mol. Cell. Biol. 7: 2745), DEAE-detran (Rosenthal, N. (1987) Methods Enzymol. 152:704-709), various liposome-based transfection reagents (Sambrook, J. et al. (1989) Molecular Cloning: A Laboratory Manual (Cold Spring Harbor Laboratory, Cold Spring Harbor, N.Y.)), and electroporation (Ausubel, F. et al. (1994) In Current Protocols in Molecular Biology (John Wiley and Sons, NY), Vol. 1, Ch. 5 and 9). Chloroquine may be added to the transfection to suppress the degradation in endosomes (Calos, M. P., 1983, Proc. Natl. Acad. Sci. USA 80: 3015). Transfection reagents include, for example, DOTMA (Roche), Superfect Transfection Reagent (QIAGEN, Cat No. 301305), DOTAP, DOPE, DOSPER (Roche #1811169), TransIT-LT1 (Miru Product No. MIR 2300), CalPhos™ Mammalian Transfection Kit (Clontech AK2051-1), and CLONfectin™ (Clontech #8020-1). Enveloped viruses in particular are known to incorporate host cell-derived proteins during virion formation, and such proteins can potentially cause antigenicity and cytotoxicity when introduced into dendritic cells (J. Biol. Chem (1997) 272, 16578-16584). It is thus advantageous to introduce dendritic cells with RNPs without the envelope (WO 00/70055).

Once an RNA virus is introduced, its viral genome is replicated within the dendritic cells, which induces the activation of dendritic cells, and differentiation into mature dendritic cells. The resulting mature dendritic cells have the ability to activate T cells. Dendritic cells introduced with RNA viruses are highly competent at activating immune system, and thus can exert anticancer effects when administered into tumors. Dendritic cells can be infected with a RNA virus in vitro (or ex vivo), for example, in desired physiological aqueous solutions, such a culture media and physiological saline. The present invention is useful in ex vivo antitumor therapy, where dendritic cells or precursor cells thereof are removed from the body, contacted with an RNA virus ex vivo, and then returned to the body after viral introduction. In the case ex vivo infection of an RNA virus, the RNA virus is preferably contacted with immature dendritic cells or mixed with a cell fraction comprising immature dendritic cells. Dendritic cells can be activated by introducing an RNA virus; however, the cells can also be activated by contacting them with bacteria, lipopolysacharide (LPS), or such. When dendritic cells are separately activated by such a method, the RNA virus may be introduced after the activation; however, to prevent any reduction in the efficiency of viral introduction, activation is preferably performed not before but after viral introduction (or at the same time as contact between the virus and dendritic cells).

For the contact of the virus with dendritic cells or progenitor cells thereof, the MOI (multiplicity of infection: the number of infecting Eves per cell) is preferably within the range of 1 to 500, more preferably within the range of 2 to 300, even more preferably within the range of 3 to 200, still more preferably within the range of 5 to 100, and yet more preferably within the range of 7 to 70. Only a short contact between the vector and dendritic cells is required, which may be, for example, one minute or longer, preferably three minutes or longer, five minutes or longer, ten minutes or longer, or 20 minutes or longer, for example, within the range of about or to 60 minutes, more specifically within the range of about five to 30 minutes. The contact time may of course be longer; for example, several days or longer.

A dendritic cell (DC) is a cell that takes a dendritic morphology in the mature state and has the ability to activate T cells by presenting an antigen. Dendritic cells include a group of bone marrow-derived cells with dendritic morphology distributed in various organs and tissues the body, and a group of cells resulting from in vitro differentiation of bone marrow- or blood-derived stem cells using cytokines or the like, that are equivalent to the cells with dendric morphology distributed in various organs and tissues in the body. Specifically, the dendritic cells include, for example, lymphocytic dendritic cells (including cells which induce Th2 or immune tolerance), bone marrow dendritic cells (generally used dendritic cells, including immature and mature dendritic cells), Langerhans cells (dendritic cells important as antigen-presenting cells in the skin), interdigitating cells (distributed in the lymph nodes and spleen T cell region, and believed to function in antigen presentation to T cells), and follicular dendritic cells (important as antigen-presenting cells for B cells; the cells present antigens to B cells by presenting antigen-antibody complexes or antigen-complement complexes on the surface via the antibody receptor or the complement receptor). Preferably, the dendritic cells highly express MHC class I and class II, and more preferably express CD11c.

A dendritic cell may also be a cell with dendritic morphology and that is positive for two or more surface markers selected from the group consisting of CD11c, HLA-class II (HLA-DR, -DP, or -DQ), CD40, and CD1a. The dendritic cells of the present invention are more preferably WA-class II$^+$ and CD11c$^+$ cells, even more preferably CD1a$^+$, HLA-class II$^+$, and CD11c$^+$ cells devoid of expression of T cell marker (CD3), B cell markers (CD 19, CD20), NK cell marker (CD56), neutrophil marker (CD15), and monocyte marker (CD14). The proportion of CD14$^+$ cells in a dendritic cell population to be used for RNA virus introduction is for example, 10% or less, preferably 5% or less, and more preferably 1% or less.

In addition, the dendritic cells of the present invention include both mature and immature dendritic cells. Immature dendritic cells refer to dendritic cells with low T cell activating ability. Specifically, immature dendritic cells may have an antigen-presenting ability that is lower than ½, preferably lower than ¼ that of dendritic cells in which maturation has been induced by adding LPS (1 μg/ml) and culturing for two days. Antigen-presenting ability can be assayed, for example, by allo T cell-activating ability (e.g., a mixed lymphocyte test: allo T cells and dendritic cells are cultured in a mixed culture with a T cell:dendritic cell ratio of 1:1 or preferably with varied ratios; $^3$H-thymidine is added eight hours before terminating cultivatic and the T cell growth capacity is assayed based on the amount of $^3$H-thymidine incorporated into the DNA of the T cells. See FIGS. 21 and 22; Gene Therapy 2000; 7; 249-254) or by the ability to induce specific cytotoxic T cells (CTLs) using a peptide (e.g., a known class I-restricted peptide of a certain antigen is added to dendritic cells; the dendritic cells are co-cultured with T cells obtained from peripheral blood of the same healthy donor from whom the dendritic cells were obtained (with 25 U/ml or preferably 100 U/ml of IL-2 on day 3 or later) (preferably stimulated by dendritic cells three times during 21 days, more preferably twice during 14 days) the resulting effector cells are co-cultured with $^{51}$Cr-labeled target cells (peptide-restricted class positive tumor cells) at a ratio of 20:1, 10:1, 5:1, or 2.5:1, preferably 100:1, 50:1, 25:1, or 12.5: for four hours; and $^{51}$Cr released from the target cells is quantified. See FIG. 23; Arch Dermat Res 292:325-332 (2000)). Furthermore, immature dendritic cells preferably have phagocytic ability for antigens, and more preferably show low (for example, significantly low as compared to mature DCs induced by LPS as described above) or negative expression of receptors that induce the costimulation for T cell activation. On the other hand, mature dendritic cells refer dendritic cells that have strong antigen-presenting ability for T cell activation or the like. Specifically, mature dendritic cells may have an antigen-presenting ability that is half or strong and preferably equivalent to or stronger than the antigen-presenting ability of dendritic cells in which maturation has been induced by adding LPS (1 μg/ml) and culturing for two days. Furthermore, mature dendritic cells preferably have weak or no phagocytic ability for antigens and more preferably show high expression of receptors that induce the costimulation for T cell activation. The activation of dendritic cells refers to the transition from immature to mature dendritic cells; activated dendritic cells encompass mature dendritic cells and dendritic cells in the process of transition wherein the expression of CD80 and CD86 that induce costimulatory signals are elevated by an activating stimuli. In CD11c positive dendritic cells, being CD83 positive serves as an indicator of mature dendritic cells.

For example, mature dendritic cells may preferably be cells whose expression of CD CD80, CD86, and HLA-class II is strongly positive. More preferably, mature dendritic cells express CD83. An immature dendritic cell can be distinguished from a mature dendritic cell by for example, using markers selected from the group consisting of CD80, CD83, and CD86. Immature dendritic cells are weakly positive for these markers, and preferably negative, while mature dendritic cells are positive.

As described above, immature dendritic cells generally have a high phagocytic ability. When dendritic cells are added with LPS (1 μg/ml) and cultured for two days, they become activated and their phagocytic ability is reduced. Phagocytic ability can be detected by measuring the amount of small molecules taken up into dendritic cells or the proportion of uptaking cells. Phagocytic ability is preferably determined by the amount of small molecules taken up into dendritic cells. For example, by using colored beads with a size of about 1 μm, the uptake of beads into dendritic cells can be measured. Quantitation is performed by subtracting the positive background at 4° C. A high phagocytic ability indicates an ability wherein the amount of small molecules taken up into dendritic cells is four times or more, more preferably five times or more, and even more preferably six times or more than that taken up into dendritic cells stimulated with LPS (1 μg/ml) for two days as described above. Alternatively, the proportion of cells taking up small molecules is twice or more, and more preferably three times or more. A low phagocytic ability is indicated when the amount of small molecules take up into dendritic cells is less than four times, more preferably less than two times, and more preferably less than 1.5 times that taken up into dendritic cells stimulated with LPS (1 μg/ml) for two days. Alternatively, when measured as the proportion of cells that take up small molecule the proportion is less than twice, and more preferably less than 1.5 times.

Those skilled in the art routinely discriminate mature dendritic cells, and each of the markers described above and methods for measuring their expression are also well known to those skilled in the art. For example, CD11c is an adhesion glycoprotein of about 150 kD (p150, integrin alpha chain). CD11c binds to CD18 to form a CD11c/CD18 complex, which is capable of binding to fibrinogen and bas been reported to function as a receptor for iC3b and ICAM-1. In addition, it has been reported that CD1c/CD18 can function as an adhesion molecule that binds to receptors on stimulated epithelia (Knapp, W. et al., eds., 1989, Leucocyte Typing IV. White Cell Differentiation Antigens, Oxford University Press, New York; Barclay, N. A. et al., eds., 1993, The Leucocyte Antigen Facts Book, CD11 Section, Academic Press Inc San Diego, Calif., p. 124; Stacker, S. A. and T. A. Springer, 1991, J. Immunol. 146:648).

CD1a is a polypeptide of about 49 kD that binds to beta microglobutin. CD1a is structurally similar to an MHC class I antigen and is assumed to function in antigen presentation (Knapp, W. et al., eds., 1989, Leucocyte Typing TV: White Cell Differentiation Antigens, Oxford University Press, New York; Schlossman, S. et al., eds., 1995, Leucocyte Typing V: White Cell Differentiation Antigens. Oxford University Press, New York; Hanau, D. et al., 1990, J. Investigative Dermatol. 95: 503; Calabi, F. and A. Bradbury, 1991, Tissue Antigens 37: 1).

CD14 is a glycosylphosphatidylinositol (GPI)-anchored single-chain glycoprotein of 53 to 55 kD expressed in dendritic reticulum cells and some types of Langerhans cells. CD14 was identified as a surface receptor with high affinity to a complex of LPS and serum LPS-binding protein (LPB) (McMichael, A. J. et al., eds., 1987, Leucocyte Typing III: White Cell Differentiation Antigens, Oxford University Press, New York, Knapp, W. et al., eds., 1989, Leucocyte Typing IV: White Cell Differentiation Antigens, Oxford University Press, New York; Schlossmin, S. et al., eds., 1995, Leucocyte Typing V: White Cell Differentiation Antigens. Oxford University Press, New York; Wright, S. D. et al., 1990, Science 249:1434).

CD40 is a type I integral membrane protein of 45 to 48 kD (type I integral membrane glycoprotein). Anti-CD40 antibody is frequently used as a cell marker (Schlossman, S. et al., eds., 1995, Leucocyte Typing V: White Cell Differentiation Antigens. Oxford University Press, New York; Galy, A. H. M.; and H. Spits, 1992, J. Immunol. 149: 775; Clark, E. A. and J. A. Ledbetter, 1986, Proc. Natl. Acad Sci. 83: 4494; Itoh, H. et al., 1991, Cell 66: 233; Barclay, N. et al., 1993, The Leucocyte Antigen Facts Book, Academic Press).

CD80 is a transmembrane glycoprotein of about 60 kD), and is a member of the Ig supergene family. CD80 is a ligand for CD28 and CD152 (CTLA-4) expressed in T cells (Schlossman, S. et al., eds., 1995, Leucocyte Typing V: White Cell Differentiation Antigens. Oxford University Press, New York; Schwarts, R. H., 1992, Cell 71: 1065; Azuma, M. et al., 1993, J. Exp. Med. 177: 845; Koulova, L. et al., 1991, J. Exp. Med. 173: 759; Freeman, G. J. et al., 1998, J. Immunol. 161: 2708, Bebrens, L. et al., 1998, J. Immunol., 161(11):5943; Guesdon J.-L. et al., 1979, J. Hitochem. Cytochem. 27: 1131-1139).

CD83 is a transmembrane protein of about 45 kD, and is a member of the Ig superfamily CD83 has a short extracellular domain of V-type Ig and a C-terminal cytoplasmic tail. CD83 mainly expressed in follicular dendritic cells, circulating dendritc cells, interdigitating dendrit cells in lymphatic tissues, in vitro-produced dendritic cells, and dendritic cells of the thymus (Zhou, L-J., and T. F. Tedder, 1995, J. Immunol. 154. 3821; Zhou, L-J. et al., 1992, J. Immunol 149: 735; Summers, K. L. et al., 1995, Clin Exp. Immunol. 100:81; Weissman, D. et al., 1995, Proc. Natl. Acad. Sci USA. 92: 826; Hart, D. N. J., 1997, Blood 90: 3245).

CD86 (B70/B7-2) is a cell surface protein of about 75 kD, which is a second ligand for CD28 and CTLA-4 and plays an important role in costimulation of T cells in early immune response (Azuma M. et al., 1993, Nature 366: 76; Nozawa Y. et al., 1993, J. Pathology 169: 3 Engle, P. et al. 1994., Blood 84: 1402, Engel, P. et al., CD86 Workshop Report. In: Leukocyte Typing V. Schlossman S. F. et al. eds., 1994, Oxford University Press; Yang, X. F. et al., 1994, Upregulation of CD86 antigen on TPA simulated U937 cells, 1994, (abstract). American Society of Hematology, Nashville, Tenn.; Guesdon, J.-L. et al., 1979, J. Histochem. Cytochem. 27: 1131-1139).

CCR7 is also called BLR-2, EBI-1, and CMKBR7, which is a seven-transmembrane protein-coupled receptor, and is a receptor of the CC chemokines, MIP-3beta/Exodus 3/ELC/CCL19 and 6Ckine/Exodus 2/SLC/TCA4/CCL21 (Sallusto, F. et al., 1999, Nature 401:708-12; Lipp, M. et al., 2000, Curr. Top. Microbiol. Immunol. 251:173-9; Birkenbach, M. et al., 1993, J. Virol. 67:2209-20; Schweickart, V. L. et al., 1994, Genomics 23:643-50; Burgstahle R. et al., 1995, Biochem Biophys. Res. Commun. 215:737-43; Yoshida, R et al., 1997, J. Biol. Chem. 272:13803-9; Yoshida, R. et al., 1998, J. Biol. Chem. 273:7118-22; Yoshida, R. et al., 1998, Int. Immunol. 10:901-10; Kim. C. H. et al., 1998, J. Immunol. 161:2580-5; Yanagihara, S. et al., 1998, J. Immunol. 161:3096-102).

DR, DP, and DQ exist as HLA-class II antigens, and can be collectively detected using anitbodies that bind to all three antigens (Pawelec, G. et al., 1985, Human Immunology 12:165; Ziegler, A. et al., 1986, Immunobiol. 171:77). HLA-DR is a human MHC class II antigen, which is a transmembrane glycoprotein consisting of an alpha chain (36 kDa) and a beta subunit (27 kDa). In epidermal Langerhans cells, the protein is co-expressed with CD1a antigen. CD1a plays a principal role in cell interaction for antigen presentation (Barclay, N. A. et al., 199. The Leucocyte Antigen Facts Book. p. 376. Academic Press).

The dendritic cells of nonhuman mammals can also be specified using the products of homologous genes of the above-described marker genes as indicators. Antibodies to such markers are commercially available, for example, from BD Biosciences (BD PharMingen), and detailed information is available at the websites of the company or its distibutors.

For dendritic cell markers, also see the references by Kietscher et al. and Oehler. (Kiertscher S M, Roth M D, Human CD14$^+$ leukocytes acquire the phenotype and function of antigen-presenting dendritic cells when cultured in GM-CSF and IL-4, J. Leukoc. Biol., 1996, 59(2):208-18; Oehler, L. et al., Neutrophil granulocyte-committed cells can be driven to acquire dendritic cell characteristics. J. Exp. Med., 1998, 187(7):1019-28). For further details regarding flow cytometry, see the references by Okano et al. and Stites et al. (Okano, S. et al., Recombinant Sendai virus vectors for activated T lymphocytes. Gene Ther., 2003, 10(16):1381-91; Stites, D. et al., Flow cytometic analysis of lymphocyte phenotypes in AIDS using monoclonal antibodies and simultaneous dual immunofluorescence., Clin. Immunol. Immunopathol., 1986, 38:161-177). The expression of each of the markers may be determine by, for example, using as a threshold the fluorescence intensity that makes a positive rate of 19 or less when stained with an isotype control antibody, wherein fluoresce equal to or above threshold is deemed positive, and fluorescence below is deemed negative.

Dendritic cells or precursor cells thereof can be prepared according to or based on known methods. For example, the cells can be isolated from blood (for example, peripheral cord blood), bone marrow, lymph nodes, other lymphatic organs, spleen, and sir. Dendritic cells to be used in the context of the present invention are preferably obtained from blood or bone marrow. Alternatively, dendritic cells to be used in the present invention may be skin Langerhans cells, veiled cells of afferent lymphatics, follicular dendritic cells, spleen dendritic cells, and interdigitating cells of lymphatic organs. The dendritic cells used in the present invention include dendritic cells selected from the group consisting of CD34$^+$-derived dendritic cells, bone marrow-derived dendritic cells, monocyte-derived dendritic cells, splenic cell-derive dendritic cells, skin-derived dendritic cells, follicular dendritic cells, and germinal center dendritic cells. CD34$^+$-derived dendritic cells can be differentiated from hematopoietic stem cells, hematopoietic progenitor cells, or the like, obtained from cord blood, bone marrow, or the like, using granulocyte colony stimulating factor (G-CSF), granulocyte macrophage colony stimulating factor (GM-CSF), tumor necrosis factor (TNF)-alpha, IL-4, IL-13, stem cell factor (SCF), Flt-3 ligand, c-kit ligand, combinations thereof, or the like. For example, peripheral blood monocytes can be differentiated into immature dendritic cells using GM-CSF and IL-4, and then differentiated into mature dendritic cells by stimulating with TNF-alpha.

When dendritic cells are selected (or enriched) from a composition including dendritic cells and other cells, it is preferable to perform so-called negative selection, which removes cells other than dendritic cells. Through the negative selection process, precursors of DC-granulocytes (J. Exp. Med., 1998, 187: 1019-1028; Blood, 1996, 87: 4520-4530) remain at thus, it is considered that not only DCs differentiated from adhesive CD14$^+$ cells, but also DCs differentiated from precursors can be recovered together. This is expected to reduce cytotoxicity.

For example, by removing T cells, NK cells, B cells, and the like, using antibodies specific thereto, dendritic cells can be enriched. Specifically, for example, it is preferable to obtain cells with low or negative expression of a surface marker selected from CD2, CD3, CD CD19, CD56, and CD66b, or any combinations thereof More preferred are cells in which the expressions of CD2, CD3, CD9, CD19, CD56, and CD66b are all low or negative. Therefore is preferable to remove cells expressing these markers by using antibodies against the markers (Hsu et al., Nature Med. 2:52 (1996)). The negative selection can be performed using polyvalent antibodies as shove in the Examples. Alternatively, a similar selection can also be performed using beads or the like for magnetic cell separation (MACS). The use of beads is preferred for large scale cell preparation, such as collection of mononuclear cells through blood cell separation or the like. For example, dendritic cells prepared by negative selection from monocytes that were enriched from a cell solution obtained from the body can be preferably u in the context of the present invention.

When dendritic cells differentiated from peripheral blood monocytes obtained from adhesive cells are selected before introduction of the RNA virus, the efficiency of virus introduction is sometimes reduced. To prevent any reduction in the proportion of immature dendritic cells, before contact with the RNA virus, cell culture is preferably carried out without the step of selecting cells adhering to a solid support (for example, a culture container such as culture dish or bottle); however the dendritic cells used in the context of the present invention are not limited thereto. Specifically, the present invention provides methods which exclude the step of selecting cells adhered to the solid support within 24 hours before contact of dendritic cells with the RNA virus. More preferably, the method excludes the step of selecting cells adhered to the solid support within two, three, five or seven days before contact of the dendritic cells with the RNA virus.

The methods preferably exclude the step of selecting CD14$^+$ cells before contact with the RNA virus, but they are not limited thereto. Specifically, the present invention provides methods that exclude the step of selecting CD14$^+$ cells within 24 hours before contact of the dendritic cells with the RNA virus. More preferably, the methods exclude the step of selecting CD14$^+$ cells within two, tree, five or seven days before contact of the dendritic cells with the RNA virus.

Specific methods for isolating dendritic cells are described in, for example, Cameron et al., Science 257:383 (1992); Landghoff et at, Proc. Natl. Acad. Sci. USA 88:7998 (1991); Chehimi et al., J. Gen. Virol. 74:1277 (1993); Cameron et al., Clin. Exp. Immunol. 88:226 (1992); Thomas et al., 1993, J. Immunol. 150:821 (1993); and Karhumaki et al., Clin. Exp. Immunol. 91:482 (1993). The isolation of dendritic cells by flow cytometry is described in, for example, Thomas et al., J. Immunol. 153:4016 (1994); Ferbas et al, J. Immunol. 152: 4649 (1994); and O'Doherty at., Immunology 82:487 (1994). In addition, magnetic cell separation is described in, for example, Miltenyi et al., Cytometry 11: 231-238 (1990).

Furthermore, for example, human dendritic cells may be isolated and grown using the methods described in Macatonia et al., Immunol. 74:399-406 (1991); O'Doherty et al., J. Exp. Med. 178:1067-1078 (1993); Markowicz et al., J. Clin. Invest. 85:955-961 (1990); Romani et al., J. Exp. Med. 180: 83-93 (1994); Sallusto et al., J. Exp. Med. 179:1109-1118 (1994); Berhard et al., J. Exp. Med. 55:1099-1104 (1995); and the like. Moreover, dendritic cells can be formed from CD34$^+$ cells obtained from bone marrow, cord blood, peripheral blood, or the like and from peripheral blood-derived mononuclear cells by the method described in Van Tendeloo et al., Gene Ther. 5:700-707 (1998).

In the present invention, it is preferable to mix an RNA virus with a cell fraction containing a high density of dendritic cells or precursor cells thereof (for example, CD11c$^+$ cell or CD34$^+$ cells). The precursor cells refer to cells that can differentiate into dendritic cells in the presence of appropriate cytokines (specifically, G-CSF, GM-CSF, TNF-alpha, IL-4, IL-13, SCF, Flt-3 ligand, or c-kit ligand, or combinations thereof). The precursor cells are preferably differentiated into dendritic cells within four weeks, more preferably within 20 days, even more preferably within 18 days, and still more preferably within 16 days. Such cells include CD34$^+$ stem cells. The differentiation into dendritic cells may be achieved, for example, by culturing the cells in the presence of SCF (50 ng/ml), GM-CSF (500 U/ml), and TNF-alpha (50 ng/ml) about 3 days, followed by culturing in the presence of SCF (50 ng/ml), GM-CSF (500 U/ml), IL-4 (250 U/ml), and TNF-alpha (50 ng/ml). A cell fraction refers to a group of cells obtained through cell separation (or cell fractionation). The cell fraction may be a composition including both cells and pharmaceutically acceptable carriers. Exemplary carriers include desired solutions that can be used to suspend viable cells, such as physiological saline, phosphate buffered saline (PBS), culture medium, and serum. According to the present methods, cell fractions to be contacted with an RNA virus include dendritic cells and/or precursors thereof at a proportion of, for example, 30% or more, preferably 40% or more, preferably 50% or more, preferably 60% or more, and preferably 70% or more to the total viable cells.

Dendritic cells to be contacted with an RNA virus preferably comprise immature dendritic cells. In a cell fraction comprising dendritic cells to be combined with an RNA virus the ratio of the number of immature dendritic cells to the number of total cells is, for example, 10% or more, preferably 20% or more, more preferably 30% or more, even more preferably 40% or more, still more preferably 50% or more, yet more preferably 60% or more, still yet more preferably 70% or more.

Anticancer agents that combine RNA viruses and dendritic cells have superior characteristics. For example, when an RNA virus is used, activated dendritic cells are obtained simply by viral infection, and the subsequent step of preparing mature dendritic cells can be omitted. Since dendritic cells need to be activated for being used to activate immunity, it is advantageous that mere viral infection can activate the cells. Furthermore, by using this property, activated T cells, such as cytotoxic T cells in particular, which are required in T cell transfer therapy, can be efficiently induced in vitro in a short time. Dendritic cells not introduced with a virus cannot induce CTL. According to previous reports on the characteristics of other viral vectors, CTL cannot be induced in vitro by merely introducing another viral vector. Thus, RNA viruses are advantageous in that T cell activation (induction CTL) can be achieved by merely introducing a virus (see FIGS. 21 to 23).

When producing the anticancer agents of the present invention, stem cells may be introduced with an RNA virus and then differentiated into dendritic cells. For example, where stem cells are differentiated into dendritic cells after being introduced with a Sendai virus, the efficiency of gene transfer reaches about 70%. This is comparable to the efficiencies of modified retroviral vectors and lentivirus vectors. Introducing adenovirus vectors into stem cells is problematic since the expression level is reduced because of episome dilution after introduction. Dendritic cells introduced with a genome-replicating RNA virus can be prepared by either a method in which stem cells are introduced with the virus and then differentiated into dendritic cells, or by a method in which genes are introduced into dendritic cells differentiated from peripheral blood mononuclear cells.

Meanwhile, when infected at higher MOIs (for example, 10 or more, preferably 20 or more, more preferably 30 or more, for example, 40 or more, or 50 or more), RNA viruses can be stably introduced into cells at almost 100% introduction efficiency vithout significant influence on cytotoxicity. RNA viruses that do not integrate their genomes into host chromosomes can also be used to advantage because of the reduced risk of tumorigenesis caused by changes in the host's genome. For this reason, RNA viruses other than retroviruses are preferably used.

The RNA viruses are not necessarily recombinant viruses. Natural RNA viruses can also be used. See "Uirusu-gaku Jikkengaku Kakuron (Special Experimental Virology), 2nd Edition (Ed. Alumnae Association of The National Institute of Health; Maruzen, 1982)" for methods for purifying and multiplying RNA viruses and methods for isolating viral strains. For example, each type of parainfluenza virus, such as a Sendai virus of Paramyxoviridae, propagates well in and can be harvested from primary culture cells of monkey kidney (MK2), human fetal lung, kidney and amnion, and trypsin-treated Vero cells (same as above, p334; Itoh H et al., Jap. J. Med. Sci. Biol. 23, 227 (1970)). The viruses cat be purified by sucrose density gradient ultracentrifugation, equilibrium centrifugation, and the like (p336). Measles virus can propagate well in various monkey cells (Matsumoto M, Bat. Rev. 30, 152 (1966)) and Vero cells are most commonly used; however, the viruses can be propagated using CV1, FL, KB, HeLa HEp2, or such (p351). For Rhabdoviridae viruses such as rabies virus, cells such as BHK, CE, Vero cells, and such are used to propagate the viruses by tissue culture methods. To purify the viruses, the pH of the culture medium three or four days after infection is adjusted to 7.4 or more and then the medium is centrifuged at low speed to remove cell debris and concentrate the viruses (p376). Arenaviridae viruses such as Lassa virus can propagate well in most culture cells passaged in vitro; however, the viruses can be propagated by culturing infected HK-21/138 cells suspended in agar (Sedwik W. D., J. Virol. 1, 1224 (1967))(p240). Togaviridae viruses such as rubella virus propagate in a wide range of culture cells, such as primary African green monkey kidney (GMK) cells, Vero, BHK21, RK13, primary quail or chicken germ cells, R66, and SIRC. BHK21 or Vero cells are commonly used to obtain a relatively high yield of viruses (p227). Orthomyxoviridae viruses such as influenza virus can propagate in embryonated hen eggs and MDCK cells (p295). The viruses can be purified by differential centrifugation, purification methods based on adsorption to and elution from erythrocytes (Lav W. G., Fundamental Techniques in Virology, 82 (1969)), or such (p317).

The RNA viruses may be viruses isolated from natural sources or created artificially by genetic recombination. Further, the viruses may have mutations and/or defects in any of the viral genes carried by the wild-type virus, as long as they retain the ability to replicate genomic RNAs in infected cells. For example, viruses that carry a mutation or defect in at least one of the genes encoding the viral envelope proteins or coat proteins can be preferably used. Such a virus can replicate its RNA genome in infected cells, however it cannot form infectious virions. Such viruses are thus highly safe, because there is no risk of spreading the infection. For example, it is possible to use minus strand RNA viruses lacking at least one of the genes encoding envelope proteins or spike proteins, such as F, H, HN, and G, or lacking any combination thereof (WO 00/70055 and WO 00/70070; Li, H.-O, et al., J. Virol. 74(14) 6564-6569 (2000)). When the genomic RNA encodes proteins required for genomic replication (for example, N, P, and L proteins), the genome can be amplified in infested cells. Specifically RNPs comprising at least N, L, and P proteins and genomic RNAs encoding these proteins, and virions comprising the RNPs are adequate as the material to be introduced into dendritic cells when producing the anticancer agents of the present invention. To produce defective-type viruses, for example, the products of defective genes, or proteins capable of complementing the defects, are exogenously supplied into virus-producing cells (WO 00/70055 and WO 00/70070; Li, H.-O. et al., J. Virol. 74(14) 6564-6569 (2000)). However, when a minus strand RNA virus carries an M protein gene, for example, non-infectious virions (VLPs) can be produced without the complementary viral proteins, because VLPs are released even if the virus does not carry the genes encoding spike proteins, such as F and HN proteins (WO 00/70070). Meanwhile, RNPs comprising genomic RNAs and N, L, and P proteins can be amplified in cells even when the virus has no envelope protein genes, and thus RNPs can be harvested from cell lysates by centrifugation or such. The antitumor agents can be produced by mixing the obtained VLPs or RNPs with desired transfection reagents and introducing the mixtures into dendritic cells.

Alternatively, the antitumor agents of the present invention can be produced using mutant RNA viruses. For example, many types of temperature-sensitive mutations in envelope proteins and coat proteins are known. RNA viruses carrying the genes for the temperature-sensitive mutant proteins can be preferably used in the present invention. Temperature-sensitive mutations refer to mutations whereby activity is significantly reduced at temperatures ordinary for the viral hosts (for example, at 37° C. to 38° C.) as compared to lower temperatures (for example, at 30° C. to 32° C.). Proteins having such a temperature-sensitive mutation are useful since they allow the production of the viruses at permissive temperatures (low temperatures).

For example, temperature-sensitive mutations in the M gene of a minus strand RNA virus include amino acid substitutions at positions arbitrarily selected from the group consisting of G69, T116, and A183 in Sendai virus M protein (Inoue, M. et al., J. Virol. 2003, 77: 3238-3246). The amino acids of homologous portions in the M proteins of other minus strand RNA virus can be easily determined: specifically, for example, the homologous position of the protein corresponding to G69 of the SeV M protein is G69 in human parainfluenza virus-1 (HPIV-1)(abbreviation is shown in parenthesis); G73 in human parainfluenza virus-3 (HPIV-3) G70 in phocine distemper virus (PDV) and canine distemper virus (CDV); G71 in dolphin molbillivirs (DMV); G70 in peste-des-petits-ruminants virus (PDPR), measles virus (MV), a rinderpest virus (RPV); G81 in Hendra virus (Hendra) and Nipah virus (Nipah); G70 in human parainfluenza virus-2 (HPIV-2); E47 in human parainfluenza virus-4a (HPIV-4a) and human parainfluenza virus-4b (HPIV-4b); and E72 in mumps virus (Mumps) (the letter and number represent an amino acid and its position, respectively). Meanwhile, the homologous position of the M protein corresponding to T116 of the SeV M protein is T116 in human parainfluenza virus-1 (HPIV-1); T120 in human parainfluenza virus-3 (PI7-3); T104 in phocine distemper virus (PDV) and canine distemper virus (CDV); T105 in dolphin molbillivirus (DMV); T104 in peste-des-petits-ruminants virus (PDPR), measles virus (MV) and rinderpest virus (RPV); T120 in Hendra virus (Hendra) and Nipah virus (Nipah); T117 in human parainfluenza virus-2 (HPIV-2) and simian parainfluenza virus 5 (SV5); T121 in human parainfluenza virus-4a (HPIV-4a) and human parainfluenza virus-4b (HPIV-4b); T119 in mumps virus Mumps); and S120 in Newcastle disease virus (NDV). The homologous position of the M protein corresponding to A183 of the SeV M protein is A183 in human parainfluenza virus-1 (HPIV-1); F187 in human parainfluenza virus-3 (HPIV-3); Y171 in phocine distemper virus (PDV) and canine distemper virus (CDV); Y172 in dolphin molbillivirus (DMV); Y171 in peste-des-petits-ruminants virus (PDPR), measles virus (MV), and rinderpest virus (RPV); Y18 in Hendra virus (Hendra) and Nipah virus (Nipah); Y184 in human parainfluenza virus-2 (HPIV-2); F184 in simian parainfluenza virus 5 (SV5); F188 in human parainfluenza virus-4a (HPIV-4a) and human parainfluenza virus-4b (HPIV-4b); F186 in mumps virus (Mumps); and Y187 in Newcastle disease virus (NDV). Viruses preferably used in the present invention are the above-mentioned viruses which comprise a genome encoding a mutant M protein comprising amino acid substitution(s) at any one of the three positions described above, preferably at two arbitrary positions of these three, and more preferably at all three positions. The amino acid mutations are preferably substitutions between amino acids whose side chains have different chemical properties. The amino acid may be substituted, for example, with an amino acid whose score in the BLOSUM62 matrix (Henikoff, S. and Henikoff, J. G. (1992) Proc. Natl. Acc. Sci. USA 89: 10915-10919) is 3 or less, preferably 2 or less, more preferably 1 or less, even more preferably 0 or less. Specifically, G69, T116, and A183 of the Sendai virus M protein, amino acids at homologous positions in the M proteins of other viruses, can be substituted with Glu (E), Ala (A), and Ser (S) respectively. Alternatively, mutations homologous to the mutations in the M protein of the temperature-sensitive mutant strain of measles virus P253-5C (Morikawa, Y. et al., Kitasato Arch. Exp. Med. 1991: 64; 15-30) can also be used. Mutations may be introduced by known mutagenesis methods, for example, by using oligonucleotides and such.

Temperature sensitive mutations of the HN gene include, for example, amino acid substitutions at positions arbitrarily selected from the group consisting of A262, G264, and K4 of the Sendai virus N protein (Inoue, M. et al., J. Virol. 2003, 77:3238-3246). Preferably, in example, A262, G264, and K461 of the Sendai virus HN protein or amino acids at homologous positions in the HN proteins of other viruses are substituted by Thr (T), Arg (R), and Gly (G) respectively. Alternatively, for example, mutations can be introduced at amino acid positions 464 and 468 of the HN protein, with reference to the temperature-sensitive mumps virus vaccine stain of Urabe AM9 (Wright, K. E. et al., Virus Res. 2000: 67; 49-57).

The minus strand RNA viruses may have mutations in their P or L gene. Specifically, such mutations include mutations of Glu at position 86 (E86) in the SeV P protein, substitutions of a different amino acid for Leu at position 511 (L511) in the SeV P protein, and substitutions homologous positions in P proteins of other minus strand RNA uses. Specifically, such mutations include substitution by Lys at amino acid position 86 and substitution by Phe at amino acid position 511. L protein mutations include the substitutions of a different amino acid for Asn at position 1197 (N1197) and/or substitutions of a different amino acid for Lys at position 1795 (K1795) in the SeV L protein, and substitutions at homologous positions in the L proteins of other minus strand RNA viruses. Specifically, such mutations include substitution by Ser at amino acid position 1197 and substitution by Glu at amino acid position 1795. P and L gene mutations can significantly potentiate the effects of persistent infectivity, suppressed release of secondary particles, or suppressed cytotoxicity. Combinations of mutations and/or defects in the envelope protein gene can also dramatically potentiate these effects.

When enveloped viruses are used, dendritic cells can be infected with viruses whose envelope comprises proteins different from the original viral envelope proteins. Viruses comprising a desired foreign envelope protein can be produced, for example, by expressing the protein in virus-producing cells at the time of virus production. Such proteins are not particularly limited, and any desired protein that confers viral infectivity to mammalian cells can be used. Specifically, for example, the proteins include vesicular stomatitis virus (VSV) G protein (VSV-G). The VSV-G protein may be derived from any VSV strain for example, VSV-G protein derived from the Indiana serotype strain can be used (J. Virology 39: 519-528 (1981)), but this is not limiting. The RNA viruses to be used in the present invention may comprise an arbitrary combination of envelope proteins derived from other viruses.

The RNA viruses may or may not encode foreign genes in their genomic RNA. Foreign genes are not necessarily required because even RNA viruses that do not encode a foreign protein will produce anticancer effects when introduced into dendritic cells. Thus, the present invention is advantageous in that desired RNA viruses, such as wild type viruses and viruses isolated from natural sources (including mutants) can be used. The RNA viruses that can be used in the present invention include, for example, RNA viruses that do not encode proteins with a therapeutic effect on cancer. Such viruses include RNA viruses that encode desired foreign proteins with no anticancer effect, for example RNA viruses encoding marker proteins, such as green fluorescence protein (GFP), luciferase, and various peptide tags, which are used to detect RNA virus introduction. Alternatively the anticancer effect can be further potentiated when a foreign gene that helps the effect is additionally integrated into the RNA viruses.

The recombinant RNA viruses carrying foreign genes can be reconstituted by known methods. Specifically, the viruses can be typically produced by the steps of:
(a) transcribing cDNAs encoding the genomic RNAs of an RNA virus in cells expressing viral proteins required for virion formation; and
(b) collecting the culture supernatant comprising the formed viruses. The viral proteins may be expressed from the transcribed viral genomic RNA or supplied in trans from a source other than the genomic RNA. When the genomic RNA lacks a viral gene required for particle formation, the viral genes are separately expressed in virus-producing cells to complement the particle formation. To express the viral proteins and RNA genome in cells, host cells are introduced with vectors in which DNAs encoding the proteins and genomic RNAs are linked downstream of an appropriate promoter that functions in the host cells. The transcribed genomic RNAs are allowed to replicate in the presence of the viral proteins, thus forming infectious virions. When defective viruses that lack genes encoding envelope proteins or such are produced, the lacking proteins, other viral proteins that can complement the function of lacking proteins, or such, are expressed in virus-producing cells.

For example, minus strand RNA viruses cam be produced by the following known methods: WO 97/16539; WO 97/16538; WO 00/70055; WO00/70070; WO 01/18223; Hasan, M. K. et al, J. Gen. Virol. 78: 2813-2820, 1997; Kato, A. et al., 1997, EMBO J. 16: 578-587; Yu, D. et al., 1997, Genes Cells 2: 457-466; Durbin, A. P. et al., 1997, Virology 235: 323-332; Whelan S. P. et al., 1995, Proc. Natl. Acad. Sci. USA 92: 8388-8392; Schnell. M. J. et al., 1994, EMBO 13: 4195-4203; Radecke, F. et al., 1995, EMBO J. 14: 5773-5784; Lawson, N. D. et at, Proc. Natl. Acad. Sci. USA 92: 4477-4481; Garcin, D. et al., 1995, EMBO J. 14: 6087-6094; Kato, A et al., 1996, Genes Cells 1: 569-579; Baron, M. D. and Barrett, T., 1997, J. Virol. 71: 1265-1271 Bridgen, A. and Elliott, R. M., 1996, Proc. Natl. Acad. Sci. USA 93: 15400-15404. These methods can reconstitute minus strand RNA viruses including parainfluenza viruses, vesicular stomatitis virus, rabies virus, measles virus, rinderpest virus, Sendai virus, and such from DNA. In the present invention, it is preferable to use minus strand RNA viruses, single-stranded minus strand RNA viruses in particular, more preferably Paramixoviridae viruses, and even more preferably viruses of the genus *Respirovirus*.

More specifically, the methods for preparing dendritic cells introduced with minus strand RNA viruses able to replicate their genome comprise introducing or transcribing the viral genomic RNAs (minus strands) or complementary strands thereof (plus strands) in to cells expressing viral proteins required for genome replication (N, P, and L). The N, P, and L proteins are supplied, for example, by introducing expression plasmids that express these proteins. Viral genomic RNA encoding the viral proteins N, P, and L) required for genome replication are used. When dendritic cells undergo this process, RNPs comprising the genomic RNA and N, P, and L are formed in the cells, and the RNPs can thus replicate autonomously in dendritic cells. In the present invention, dendritic cells introduced with minus strand RNA viruses can be prepared by forming viral RNPs directly in dendritic cells, as described above. When cells other than dendritic cells are used, the formed RNPs and infectious or non-infectious virions are harvested. When M protein is present its action causes virions (or VLPs) to be released from cells. When spike proteins (for example, F and HN (or H) proteins, G protein, or the like) are also present, these spike proteins are incorporated into the formed particles and the virions become infectious as a result. In the absence of spike proteins but presence of M protein, non-infectious virions (VLPs) are released. The harvested RNPs or VLPs are introduced into dendritic cells, for example, along with transfection reagents or the like. Dendritic cells can be infected by directly adding the infectious virions to the cells. Dendritic cells introduced with a minus strand RNA virus can be produced by this procedure.

Methods for producing plus (+) strand RNA viruses include the following examples:

(1) Coronavirus
Enjuanes L, Sola I, Aonso S, Escors D, Zuniga S.
 Coronavirus reverse genetics and development of vectors for gene expression.
 Curr Top Microbiol Immunol. 2005;287:161-97. Review.
(2) Togavirus
Yamanaka X, Zullo S A, Ramsey J, Onodera M, Tanaka R, Blaese M, Xanthopoulos K G.
 Induction of therapeutic antitumor antiangiogenesis by intratumoral injection of genetically engineered endostatin-producing Semliki Forest virus.
 Cancer Gene Ther. 2001 October; 8(10):796-802.
Datwyler D A, Eppenberger H M, Koller D, Bailey J E, Magyar J P.
 Efficient gene delivery into adult cardiomyocytes by recombinant Sindbis virus.
 J Mol Med. 1999 December; 77(12):859-64.
(3) Picornavirus
Lee S C, Kim D Y, Hyun B H Bae Y S.
 Novel design architecture for genetic stability of recombinant poliovirus: the manipulation of G/C contents and their distribution patterns increases the genetic stability of inserts in a poliovirus-based RtPS-Vax vector system J Virol. 2002 February; 76(4):1649-62.

Mueller S, Wimmer E.

Expression of foreign proteins by poliovirus polyprotein fusion: analysis of genetic stability reveals rapid deletions and formation of cardioviruslike open reading frames.

J Virol. 1998 January; 72(1):20-31.

(4) Flavivirus

Yin S, Kim S Y, Rice C M, Lee Y M.

Development and application of a reverse genetics system for Japanese encephalitis virus.

J Virol. 2003 June; 77(11):6450-65.

Arroyo J, Guirakhoo F, Fenner S, Zhang Z X, Monath T P, Chambers T J.

Molecular basis for attenuation of neurovirulence of a yellow fever Virus/Japanese encephalitis virus chimera vaccine (ChimeriVax-JE).

J Virol. 2001 January; 75(2):934-42.

(5) Reovirus

Roner M R, Joklik W K.

Reovirus reverse genetics: Incorporation of the CAT gene into the reovirus genome.

Proc Natl Acad Sci USA. 2001 Jul. 3; 98(14):803641. Epub 2001 Jun. 26.

For methods of multiplying other RNA viruses and preparing recombinant viruses, see Uirusu-gaku Jikkengaku Kakuron, 2nd Edition (E. Alumnae Association of The National Institute of Health; Maruzen, 1982).

The foreign genes carried by the RNA viruses are not particularly limited; they include genes of natural proteins, for example, hormones, cytokines, growth factors, receptors, intracellular signaling molecules, enzymes, antibodies (including complete antibodies, antibody fragments, such as Fab, and single chain antibodies), peptides, and such. The proteins may be secretory proteins, membrane proteins, cytoplasmic proteins, nuclear proteins, and the like. Artificial proteins include, for example, fusion proteins, such as chimera toxin, dominant negative proteins (including soluble receptor molecules and membrane-bound dominant negative receptors), and truncated forms of cell adhesion molecules and cell surface molecules. The proteins may also be proteins additionally comprising a secretory signal, membrane localization signal, nuclear translocation signal, or such. The functions of a particular gene can be suppressed by expressing an antisense RNA molecule or RNA-cleaving ribozyme as the introduced gene. The anticancer effect can be potentiated by preparing the virus using a therapeutic gene showing anticancer effect as the foreign gene.

For example, the anticancer effect can be potentiated by expressing genes that inhibit angogenesis or vascular formation in dendritic cells. Genes known to enhance neovascularization or vascular formation include, for example, fibroblast growth factor 2 (FGF2) Baffour, R. et al., J. Vasc. Surg. 16(2):181-91, 1992), endothelial cell growth factor (ECGF; Pu, L. Q. et al., J. Surg. Res. 54(6):575-83, 1993), vascular endothelial growth factor/vascular permeability factor (VEGF/VPF; Takeshita, S. et al., Circulation 90(5 Pt 2):II228-34, 1994; Takeshita, S. et al., J. Clin. Invest. 93(2): 662-70, 1994), and hepatocyte growth factor/scatter factor (HGF/SF). Genes encoding secretary proteins that inhibit the activities of these signaling molecules can be expressed in dendritic cells. Specifically, such proteins include antibodies that bind to these signaling molecules or to their receptors, or polypeptides comprising antigen-bound fragments thereof, and soluble proteins of those receptors (secreted receptors that comprise a ligand-binding domain but not a transmembrane domain). In particular, the effect of suppressing cancer growth can be significantly potentiated by introducing dendritic cells with an RNA virus encoding a soluble polypeptide of FGF receptor (FGF-R). Thus, RNA viruses encoding soluble FGF-R can be preferably used in the present invention. The soluble FGF-R may be natural soluble FGF-R or a fragment comprising an extracellular domain of a membrane-bound FGF-R (FGF-R1 and such) (A. Hanneken and A. Baird, Investigative Ophthalmology & Visual Science, Vol 36, 1192-1196, 1995; Takaishi, S. et al, Biochem Biophy Res Commun., 267(2):658-62, 2000; Seno M, et al., Cytokine, 10(4):290-4, 1998; Hanneken, A FEBS Lett. 489:176, 2001).

Dendritic cells can present cancer antigen peptides expressed in a target cancer. Such antigens to be presented by dendritic cells can be encoded by RNA viruses, added (i.e., pulsed) to dendritic cells introduced with RNA viruses, or expressed using an alternative desired vector. Tumor antigens are preferably specific to tumor cells (i.e., exist in tumor cells but not in non-tumor cells), but may be antigens that are more abundant in tumor cells than in the same type of non-tumor cells. The tumor antigens may be complete cancer antigen proteins or partial peptides thereof Once the peptide presented by the dendritic cells is identified, the peptide can be synthesized and used. The immune response is induced when the antigen peptide is presented on the surface of dendritic cells as a result of binding to the MHC molecule on the cell surface.

When CTL acts as a major effector, a desired intercellular or extracellular tumor antigen can be used. When an antibody is reacted as the effector by using dendritic cells to activate CD4 T cells which triggers the induction of antibody production through B cell activation, it preferred to use antigens presented on the cell surface. For example, a cell surface receptor cell adhesion protein can be used as the antigen. The tumor antigens include, for example Muc-1 or Muc-1-like mucin tandem repeat peptide that induce ovarian cancer or the like (U.S. Pat. No. 5,744,144); E6 and E7 proteins of human papilloma virus, which cause cervical cancer; melanoma antigens MART-1, MAGE-1, -2, -3, gp100, and tyrosinase; prostate cancer antigen PSA; as well as CEA (Kim, C. et al., Cancer Immunol. Immunother 47 (1998) 90-9 and Her2neu (HER2p63-71, p780-788; Eur J. Immunol. 2000; 30: 3338-3346).

In addition, by expressing a cytokine in dendritic cells, the cells stimulate the immune system, thereby enhancing immune responses against cancers. Thus, dendritic cells introduced with a gene encoding a cytokine are also useful. A dendritic cell introduced with an RNA virus carrying a gene encoding an immunostimulatory cytokine serves as an effective agent for inducing tumor immunity. For example, immunostimulatory cytokines include interleukins (for example, IL-1alpha, IL-1beta, IL-2, IL-3, IL-4, IL-6, IL-7, IL-8, IL-9, IL-10, IL-12, IL-15, IL-1 IL-19, IL-20, IL-21, IL-23, and IL-27), interferons (for example, IFN-alpa, IFN-beta, and IFN-gamma), tumor necrosis factor (TNF), transforming growth factor (TGF)-beta, granulocyte colony stimuli factor (G-SF), macrophage colony stimulating factor (M-CSF), granulocyte macrophage colony stimulating factor (GM-CSF), insulin-like growth factor (IGF)-1, IGF-2, Flt-3 ligand, Fas ligand, c-kit ligand, and other immunomodulatory proteins (such as chemokine and costimulatory molecules).

The amino acid sequences of these cytokines are well known to those skilled in the art. One may refer to: for IL-4, for example, Arai et al. (1989), J. Immunol. 142(1) 274-282; for IL-for example, Yasukawa et al (1987), EMBO J., 6(10): 2939-2945; for IL-12, for example, Wolf et al. (1991), J. Immunol. 146(9): 3074-3081; for IFN-alpha, for example, Gren et al. (1984) J. Interferon Res. 4(4): 609-617, and Weismann et a. (1982) Princess Takamatsu Symp. 12: 1-22. IFN-beta includes, for example, sequences containing the sequence of positions 139 to 636 of Accession number NM_002176 (corresponding to positions 22 to 187 of the amino acid sequence of NP_002167). In addition, one may refer to: for TNF, for example, Pennica et al. (1984) Nature 312: 724-729; for G-CSF, for example, Hirano et al. (1986) Nature 324:73-76; and for GM-CSF, for example, Cantrell et al. (1985) Proc. Natl. Acad. Sci. (USA) 82(18): 6250-6254. More specifically, the nucleic acid sequence encoding GM-CSF includes sequences containing the sequences from positions 84 to 461 of Accession number NM_000758 (corresponding to positions 18 to 144 of the amino acid sequence of NP_000749). The nucleic acid sequence encoding IL-4 includes sequences containing the sequences from positions 443 to 829 of Accession number NM_000589 (corresponding to positions 25 to 153 of the amino acid sequence of NP_000580). Signal peptide sequences may be appropriately substituted with those of other proteins. Natural genes encoding these cytokines and the degeneracy of genetic code can be used to design mutant genes that encode functional cytokines, which can be introduced into dendritic cells.

The genes may also be modified to express modified forms of the cytokines. For example, a cytokine that has two forms, a precursor form and matured form (for example, those producing active fragments by cleavage of their signal peptides, or by restrictive proteolysis), may be genetically modified to express either the precursor or the matured form. Other modified forms (for example, fusion proteins of an active fragment of a cytokine and a heterologous sequence (for example, heterologous signal peptide)) can also be used.

If required, dendritic cells introduced with RNA viruses can be combined with desired pharmaceutically acceptable carriers or media (for example, physiological saline, Ringer's solution, culture medium, or serum). If required, the cells may be concentrated by centrifugation and then re-suspended in a physiological solution, such as culture medium or physiological saline. Such dendritic cells prepared according to the present invention are useful in immune therapies effective against cancers. Immune sensitization mediated with dendritic cells introduced with a gene encoding such a tumor antigen or T cells stimulated with the dendritic cells is an effective method to induce antitumor effect in patients. The present invention relates to uses of dendritic cells obtained by the methods of present invention in anticancer treatment. The present invention also relates to uses of dendritic cells obtained by the methods of present invention in producing anticancer agents (or carcinostatic agents, agents for suppressing cancer growth, and such). The present invention also relates to uses of RNA viruses and dendritic cells in producing anticancer agents (or carcinostatic agents, agents for suppressing cancer growth and such).

The resulting dendritic cells are useful as DC vaccines. To enhance antigenicity, immunostimulants, such as cytokines, cholera toxins, or Salmonella toxins, can be added to dendritic cells introduced with RNA viruses. In addition, adjuvants can also be combined, such as alum, incomplete Freund's adjuvant, MF59 (oil emulsion), MTP-PE (muramyl tripeptide derived from Mycobacterial cell wall), and QS-21 (derived from soapbark tree *Quilaja saponaria*).

The present invention also relates to packages comprising the RNA viruses and dendritic cells, wherein the packages comprise a description of the use of the dendritic cells to suppress cancers. The RNA viruses and dendritic cells may be arranged separately in different containers, or together in a single container. The present invention also relates to packages comprising dendritic cells introduced with RNA viruses, wherein the packages comprise a description of the use of the dendritic cells to suppress cancers. The RNA viruses and dendritic cells may be suspended in solutions, such as culture medium or physiological saline. The phrase "use to suppress cancers" means, for example, that dendritic cells introduced with RNA viruses or compositions comprising them are used as anticancer agents or to suppress tumor growth, to regress cancers, to treat cancers, to treat cancer patients, or to prolong patients' lives. Such descriptions may be printed directly on the packages, or the packages may contain a sheet of paper or a sticker comprising the description. The packages may be containers that contain the RNA viruses and/or dendritic cells; in this case, the containers may be, for example, bottles, tubes, vinyl bags, vials, and syringes. Alternatively, the packages of the present invention may comprise bags, cases, or such to place the containers in. The packages may also comprise instructions recording the methods for administering dendritic cells, and can further comprise syringes, catheters, and/or needles and such for use in administering the dendritic cells.

Since the anticancer agents produced according to the present invention are introduced into the body, they are safer when the dendritic cells they comprise have lost the ability to grow. For example, induction of differentiation is known to drastically reduce the ability of cord blood-derived monocytes to grow. For safer use as a cell vaccine, the cells can be treated by heating, radiation, mitomycin C, or such, so that their ability to grow is lost but their function as a vaccine is retained. For example, when treated with X-ray radiation, the cells can be irradiated at a total dose of 1000 to 3300 Rad. When mitomycin C treatment is used, for example, mitomycin C can be added to dendritic cells at a concentration of 25 to 50 micro-g/ml and the mixture can be incubated at 37° C. for 30 to 60 minutes. When treating cells using heat treatment, for example, the cells can be heated at 50° C. to 65° C. for 20 minutes.

When dendritic cells are administered, it is effective to use combinations of cytokines that boost the adjuvant effect. Such genes include, for example:

(i) combination of IL-2 and single-chain IL-12 (Proc. Natl. Acad. Sci. USA 96 (15): 8591-8596, 1999);

(ii) IL-2 and interferon-γ (U.S. Pat. No. 5,798,100);

(iii) granulocyte-colony stimulating factor (GM-CSF) alone; and (iv) combinations of GM-CSF and IL-4 (J. Neurosurgery 90 (6), 1115-1124 (1999)).

Dendritic cells introduced with RNA viruses are useful for stimulating the T cells of patients themselves in vivo, and are also useful for stimulating T cells in vitro. A patient's tumor immunity can be stimulated by ex vivo immune therapy where the sensitized T cells are administered to the patients.

The present invention relates to methods for producing anticancer agents comprising T cells that were stimulated by dendritic cells, which comprise the steps of:

(a) introducing an RNA virus into dendritic cells or precursor cells thereof;

(b) differentiating the cells into mature dendritic cells;

(c) allowing the mature dendritic cells to present a cancer antigen; and (d) contacting T cells with the mature dendritic cells.

Dendritic cells introduced with RNA viruses activate T cells, thereby inducing CTLs. The antigens to be presented by the dendritic cells may be cancer antigens expressed from RNA viruses (or processed products thereof), or dendritic cells may be pulsed exogenously with the antigens. The resulting T cells can be used for cancer therapy. When T cells and dendritic cells are contacted in vitro, the dendritic cells are preferably contacted with T cells collected from patients and then the T cells are administered ex vivo.

The present invention also relates to methods for suppressing cancers using dendritic cells prepared by the methods of the present invention. For example, treatments that stimulate antitumor immunity in cancer patients can be carried out. These methods comprise the step of administering dendritic cells. Specifically, the methods comprise the step of administering patients with a therapeutically effective dose of dendritic cells carrying an RNP complex of an RNA virus able to replicate its genome. These methods are expected to suppress cancer growth as compared to cases where the dendritic cells of the present invention are not administered. The RNA viruses may not carry foreign genes, or may carry genes encoding one or more cancer antigens, immunostimulatory cytokines, proteins that inhibit angiogenesis, and the like. Since dendritic cells are activated when introduced with an RNA virus, a patient's immune system against cancers can also be activated even when dendritic cells introduced with an RNA virus not carrying a foreign gene are administered to cancers. Dendritic cells having stronger cancer-suppressing effects can be prepared by pulsing the dendritic cells with a cancer antigen peptide, then allowing the dendritic cells to present the desired antigen.

The present invention is applicable to any solid cancers. Such cancers include, for example, tongue cancer, gingival cancer, malignant lymphoma, malignant melanoma, maxillary cancer, nose cancer, nasal cavity cancer, laryngeal cancer, pharyngeal cancer, glioma, meningioma, glioma, lung cancer, breast cancer, pancreatic cancer, gastrointestinal carcinoma (esophageal cancer, gastric cancer, duodenal cancer, colorectal cancer), squamous cell carcinoma adenocarcinora, alveolar cell carcinoma, testicular tumor, prostatic cancer, thyroid cancer, hepatocarcinoma, ovarian cancer, rhabdomyosarcoma, fibrosarcoma, osteosarcoma, and chondrosarcoma. Target cancers are preferably epithelial cancers, more preferably skin cancer including squamous cell carcinomas of the skin, basal cell carcinomas of the skin, Bowen's disease of the skin, Paget's disease of the skin, and malignant melanomas of the skin.

Dendritic cells introduced with RNA viruses are generally administered to cancer lesions in patients at a dose of $10^5$ to $10^9$ cells, preferably $10^6$ to $10^8$ cells, and more preferably about $10^7$ cells. A cancer lesion refers to cancer tissue or surrounding area (for example, area with a radius of 5 mm or less, and preferably 3 mm or less, from the cancer). The dose can be appropriately adjusted according to the type and stage of cancer, the presence of introduced genes, and such, RNA viruses not carrying a foreign gene can still produce an antitumor effect however a stonger effect can be produced when the RNA virus carries an IFN-beta gene, a gene for soluble FGF receptor, or such. Alternatively, a stronger effect can be produced when a tumor antigen is contacted with dendritic cells before the cells are administered to a tumor. Contact between a tumor antigen and dendritic cells can be achieved using methods such as mixing dendritic cells with a tumor cell lysate, pulsing dendritic cells with a tumor antigen peptide; or introducing and expressing a tumor antigen gene in dendritic cells. Alternatively, the antitumor effect can be produced by directly injecting cancer lesions with the dendritic cells of the present invention along with IFN-beta, soluble FGF receptor, or a desired vector carrying a gene encoding either of these genes. Specifically, in the present invention it is preferable to combine the administration of dendritic cells introduced with an RNA virus, with antitumor treatment using IFN-beta or soluble FGF receptor.

When T cells activated with the dendritic cells are administered, for example, the T cell can be administered by intravenous injection at a dose of about $10^5$ to $10^9$ cells, preferably $10^6$ to $10^9$ cells, and more preferably $10^8$ to $10^9$ cells per 1 m$^2$ body surface area (see Ridell et al., 1992, Science 257:238-241). The injection can be repeated at desired intervals (for example, monthly). Administered recipients may be monitored for any side effects during or after T cell injection, if required. In this case, the T cells are preferably obtained from the same patient from whom the dendritic cells were derived. Alternatively, the T cells may be collected from a patient, while the dendritic cells to stimulate the T cells may be derived from an HLA-compatible healthy donor. Conversely, the dendritic cells may be collected from a patient while the T cells may be derived from an HLA-compatible healthy donor.

The number of times dendritic cells or T cells are administered may be once or several times as long as side effects are clinically acceptable. The daily administration frequency is also determined in a similar way. The administered subjects are not particularly limited, and include birds and mammals (human and nonhuman mammals), for example, chickens, quails, mile, rats, dogs, pigs, cats, bovines, rabbits, sheep, goats, monkeys, and humans. When administered to animals other than humans, the cells may be administered, for example, at a dose calculated from the doses described above and based on the weight ratio between the subject animal and human.

EXAMPLES

Hereinbelow, the present invention is specifically described in the context of Examples however, it is not to be construed as being limited thereto. All publications cited herein are incorporated as a part of the specification.

A. Examination of Introduction Efficiency:

[Experiment 1]

Monocytes from healthy donors were enriched by negative selection. A RosettSep™-human monocyte enrichment cocktail (Stem Cell Technology Inc.) was used in the negative selection to enrich the monocytes. Specifically, a tetrameric antibody (an antibody consisting of two antibody molecules linked together: one is anti-glycophorin A antibody that recognizes erythrocytes, and the other is an antibody that recognizes a surface antigen of mononuclear cells) was used to bind cells to be removed to erythrocytes, and the cells were removed using Ficoll Paque™ Plus (Pharmacia Biotech Inc.). This negative selection eliminated cells expressing CD2, CD3, CD8, CD19, CD56, and CD66b, and the remaining cells were used as monocyte-enriched cells in the following induction of DC differentiation. At this stage, 65-80% were $CD14^+$ cells. GM-CSF (500 U/ml) and IL-4 (250 U/ml) were added to the monocyte-enriched cells, and the cells were cultured in endotoxin-free RPMI supplemented with 10% FCS to prepare DCs. After three to four days, half of the culture supernatant was exchanged with fresh culture medium of the same composition. The cells were confirmed to have positive expression of the costimulatory molecules, and of CD11c, HLA-class II (DR, DP, and DQ), and CD1a, and not to present other lineage markers (CD3, CDS6, CD19, CD15, and CD14) (FIG. 1, and data not shown). These cells were used to test the efficiency of viral introduction. At this stage, 90% to 98% of die viable cells expressed DC markers (CD11c and HLA-class II (DR, DP, and DQ)).

Although the above-described kit was used for the selection in this Example, similar selections can also be performed by using antibody-coated magnetic beads. The use of beads is preferred when preparing cells on a large scale, such as when collecting mononuclear cells through blood cell separation or the like.

[Experiment 2]

Figure 6:
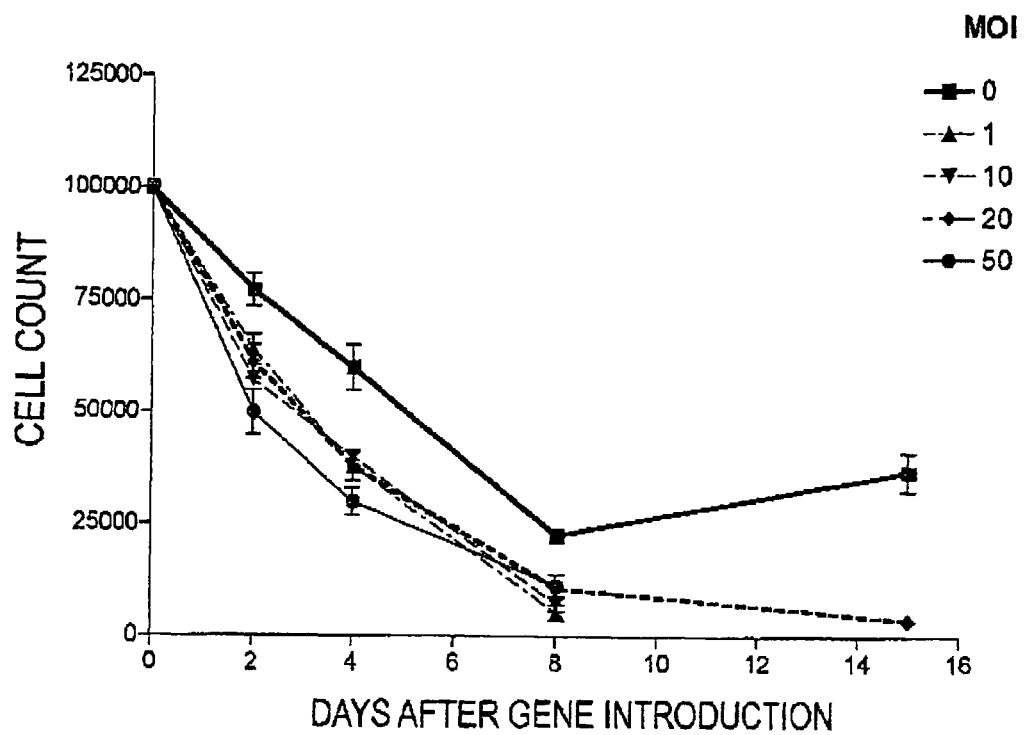
FIG. 6 depicts a graph showing alterations in DC count after introduction of a GFP-expressing RNA virus.

Sendai virus Z strain (SeV-GFP) (transmissible; WO 00/70070) expressing green fluorescent protein (GFP) was infected to the DCs obtained in Experiment 1 (seven days after differentiation induction) at various MON. Changes in the cell count, GFP expression level, and the expression levels of the costimulatory molecules were investigated over time. The results showed that % GFP reached a maximum level when the MOI was 20 or greater (FIGS. 2 to 5). The mean fluorescence intensity (MFI) of GFP can be further increased when the MOI is increased to 100 (data not shown). The MFI of GFP increased up to day 8. The level of costimulatory molecules (CD80 and CD86) as a whole was maximized when the MOI was 20 or greater. Regarding decreases in cell count, hardly any change was observed for MOIs of 1 to 20, and a slight decrease was observed at an MOI of 50, but this was not significant (FIG. 6).

[Experiment 3]

Figure 7:
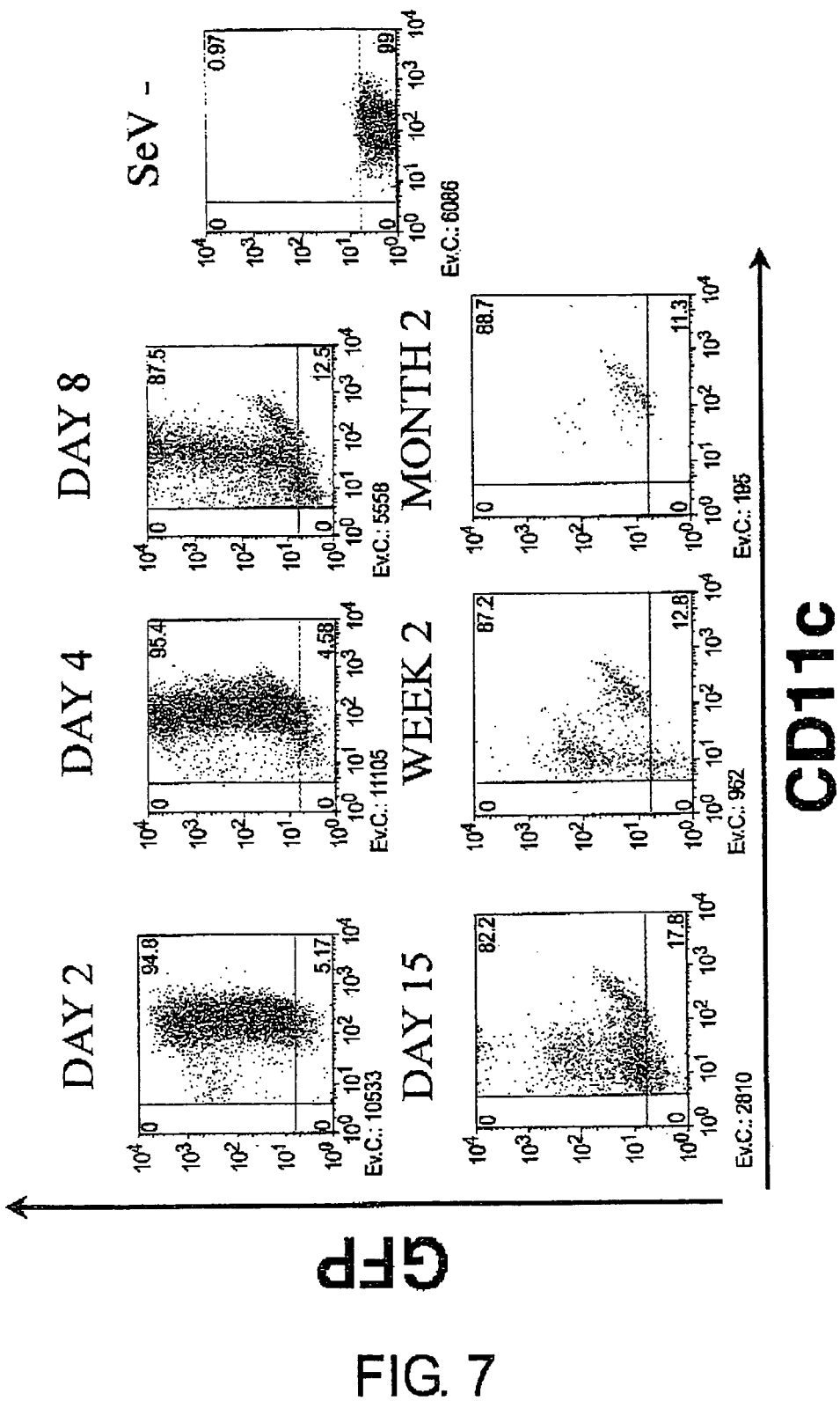
FIG. 7 depicts graphs showing the duration of GFP expression after introduction of a GFP-expressing RNA virus.

The DCs were infected with SeV-GFP at an MOI of 20, and the GFP expression was examined over time using FACS. The results showed that expression decreased after two weeks (cell count also decreased), but GFP-expressing cells were detectable up to two months later (FIG. 7). As described in the Example below, DCs are activated by infection with an RNA virus. Thus, gene transfer into DCs using an RNA virus is clinically applicable to vaccination. Administration can be in vivo or ex vivo; however, for example, gene expression can be maintained in the body for a long period if DCs infected with an RNA virus are frequently administered using ex vivo administration.

[Experiment 4]

Figure 8:
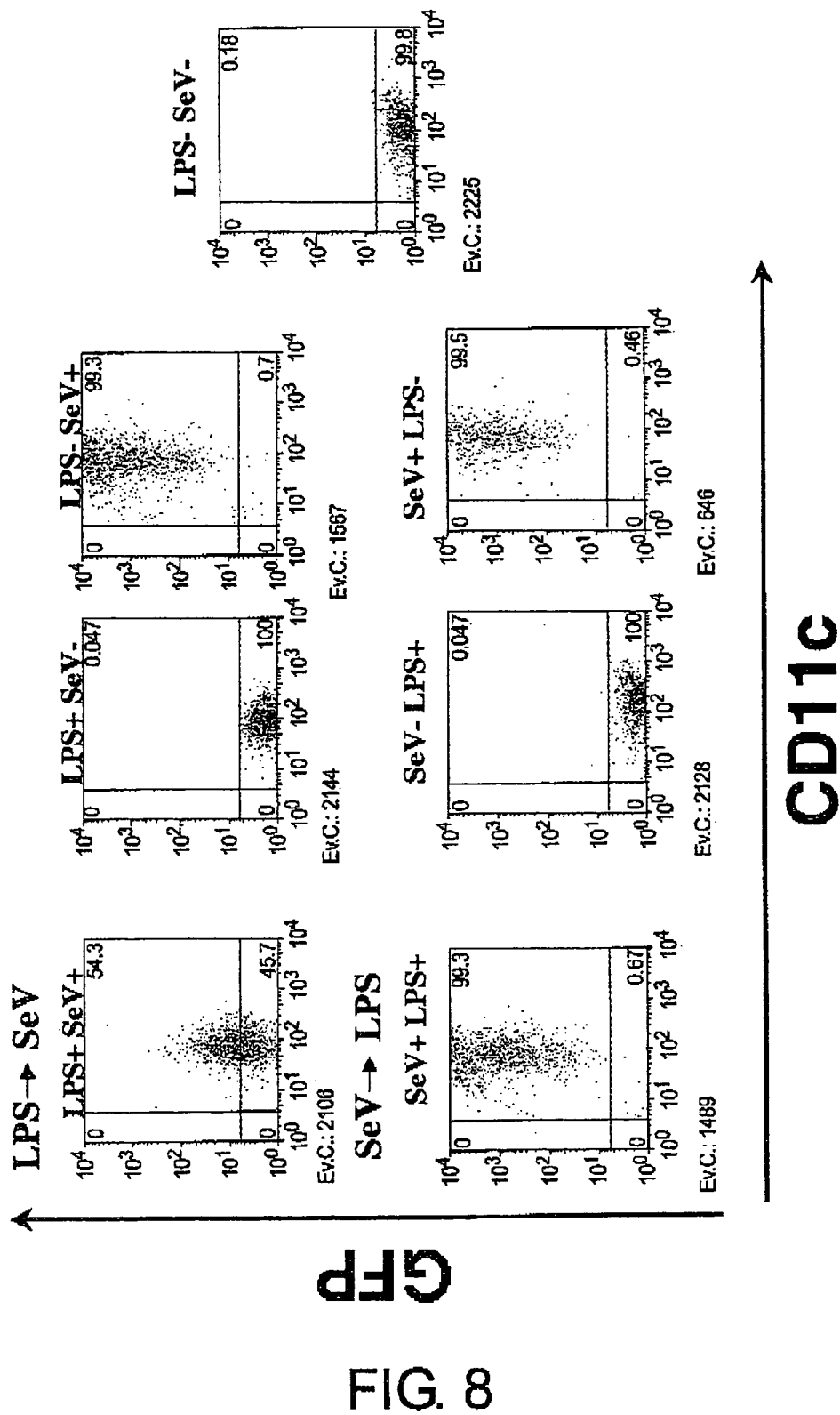
FIG. 8 depicts graphs showing the effect of LPS stimulation on the introduction efficiency of a GFP-expressing RNA virus into human DCs.
Figure 9:
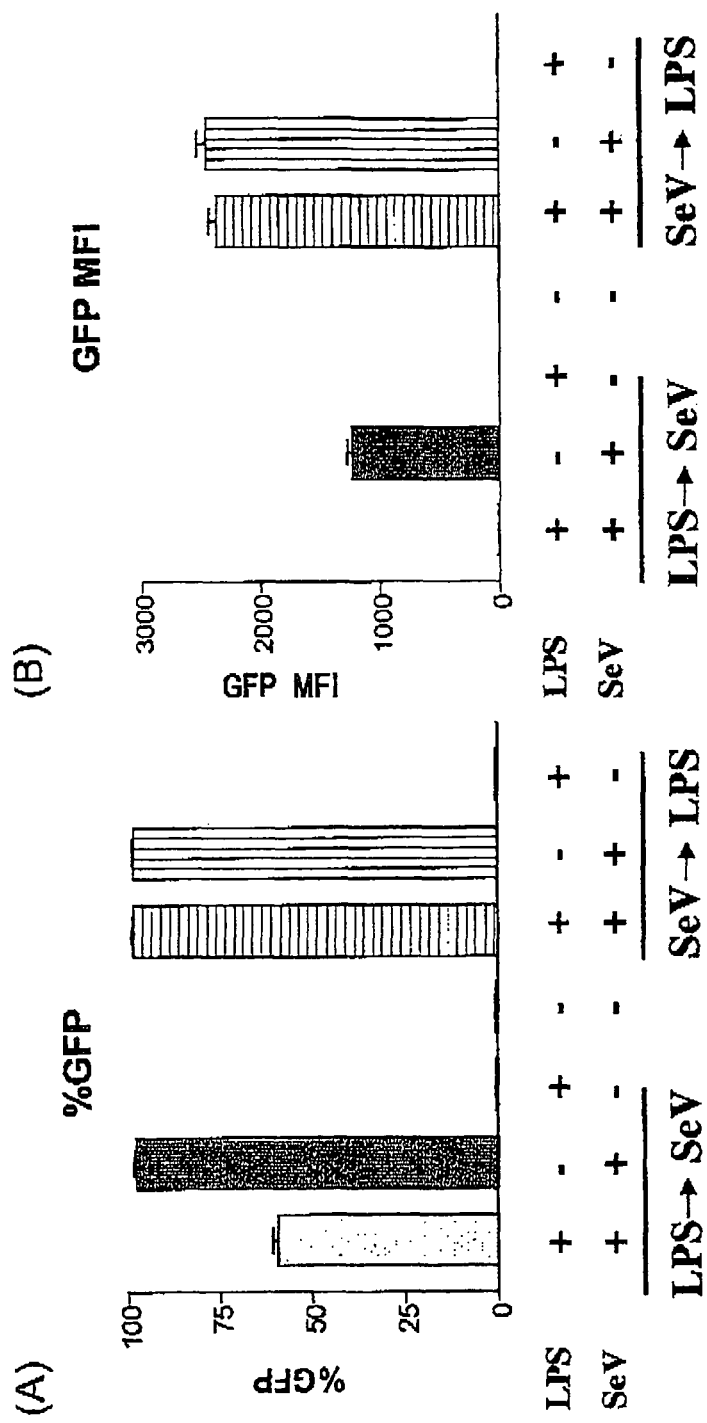
FIG. 9 depicts graphs showing the effect of LPS stimulation on the introduction efficiency of a GFP-expressing RNA virus into human DCs.

Activation and infection efficiencies were examined. The change in viral infection efficiency due to activation was examined. DCs cultured for seven days were stimulated with LPS (1 μg/ml) for two days, infected with SeV-GFP at an MOI of 30, and after two days GFP was analyzed by FACS. Alternatively, two days after SeV-GFP infection, LPS stimulation was carried out under the same conditions (for two days). (FIGS. 8 and 9).

Results: % GFP of the human DCs was found to be nearly 60% positive after activation with LPS. In contaast, in mouse DCs, the positivity rate was very low (data not shown). However, MFI was also very low in humans, showing a drastic decrease in the efficiency of gene transfer into DCs after activation. In contrast, gene transfer efficiency was not altered by LPS stimulation after SeV introduction. These results demonstrate that it is preferable to use immature DCs, i.e. non-activated DCs, for obtaining DCs introduced with an RNA virus.

[Experiment 5]

Figure 10:
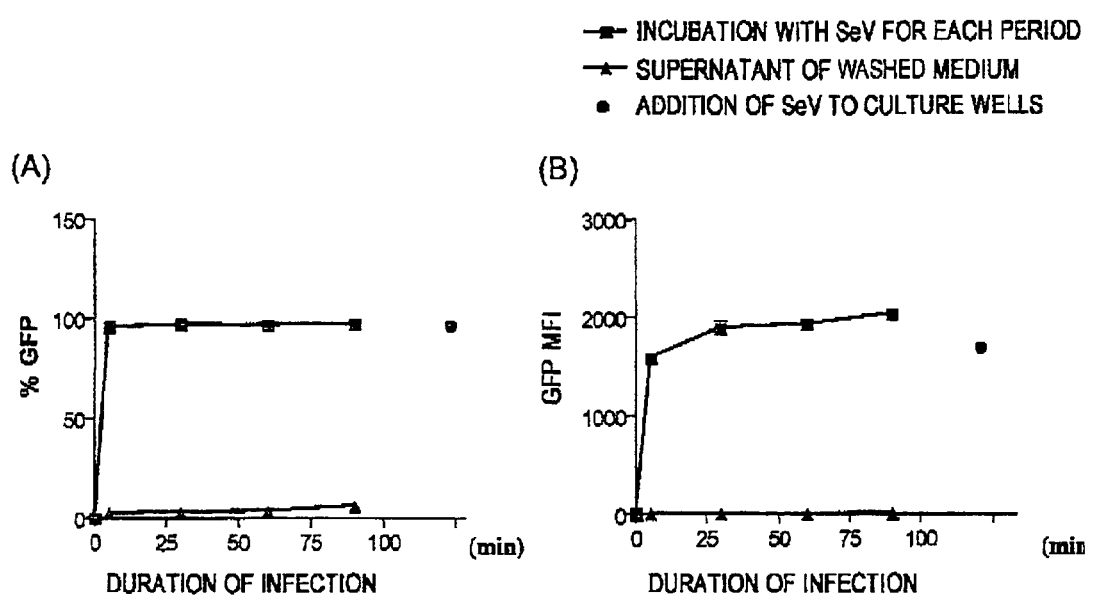
FIG. 10 depicts graphs showing the results of examining the incubation time for gene transfer into DCs.

The contact time required for infection was examined (FIG. 10). The results demonstrate that gene transfer can be achieved in about 30 minutes or less.

[Experiment 6]

Figure 11:
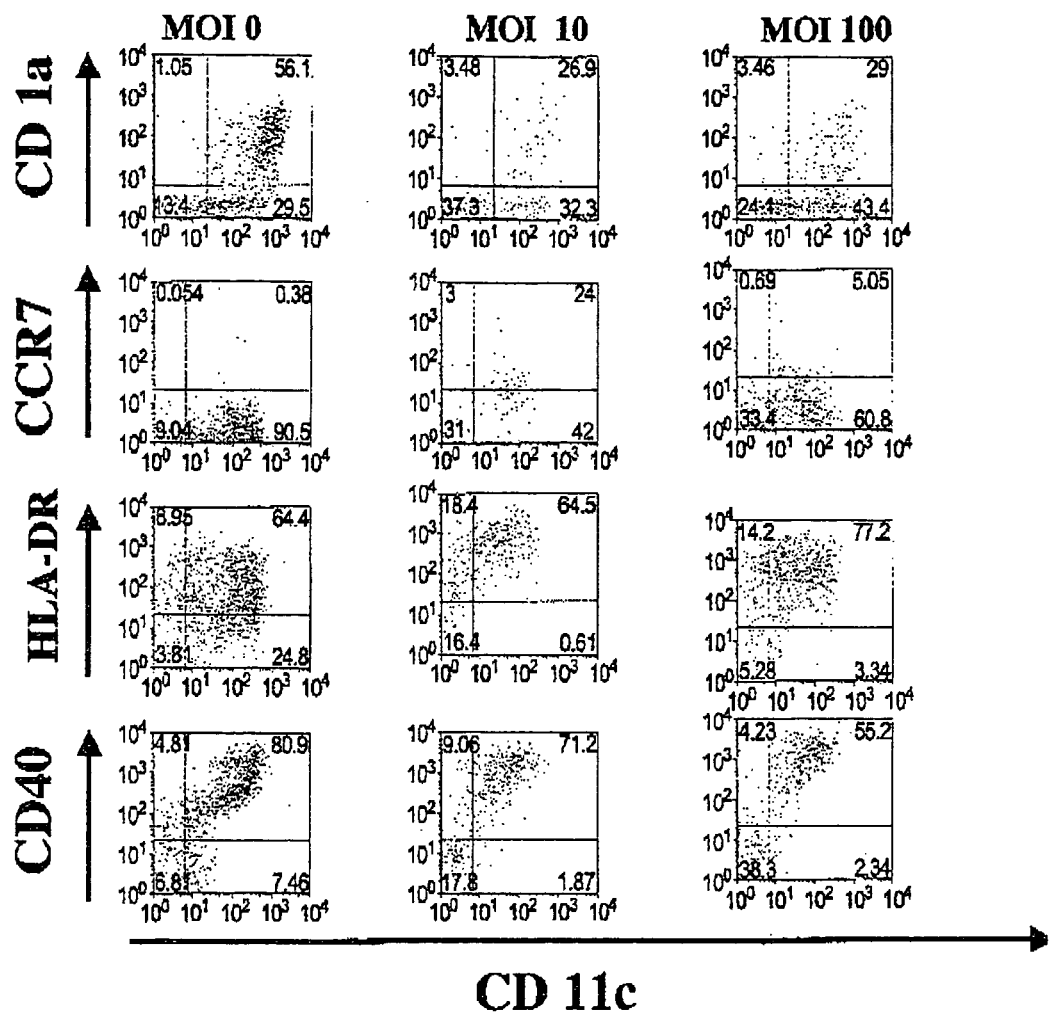
FIG. 11 depicts graphs showing gene transfer into DCs derived from cord blood.
Figure 12:
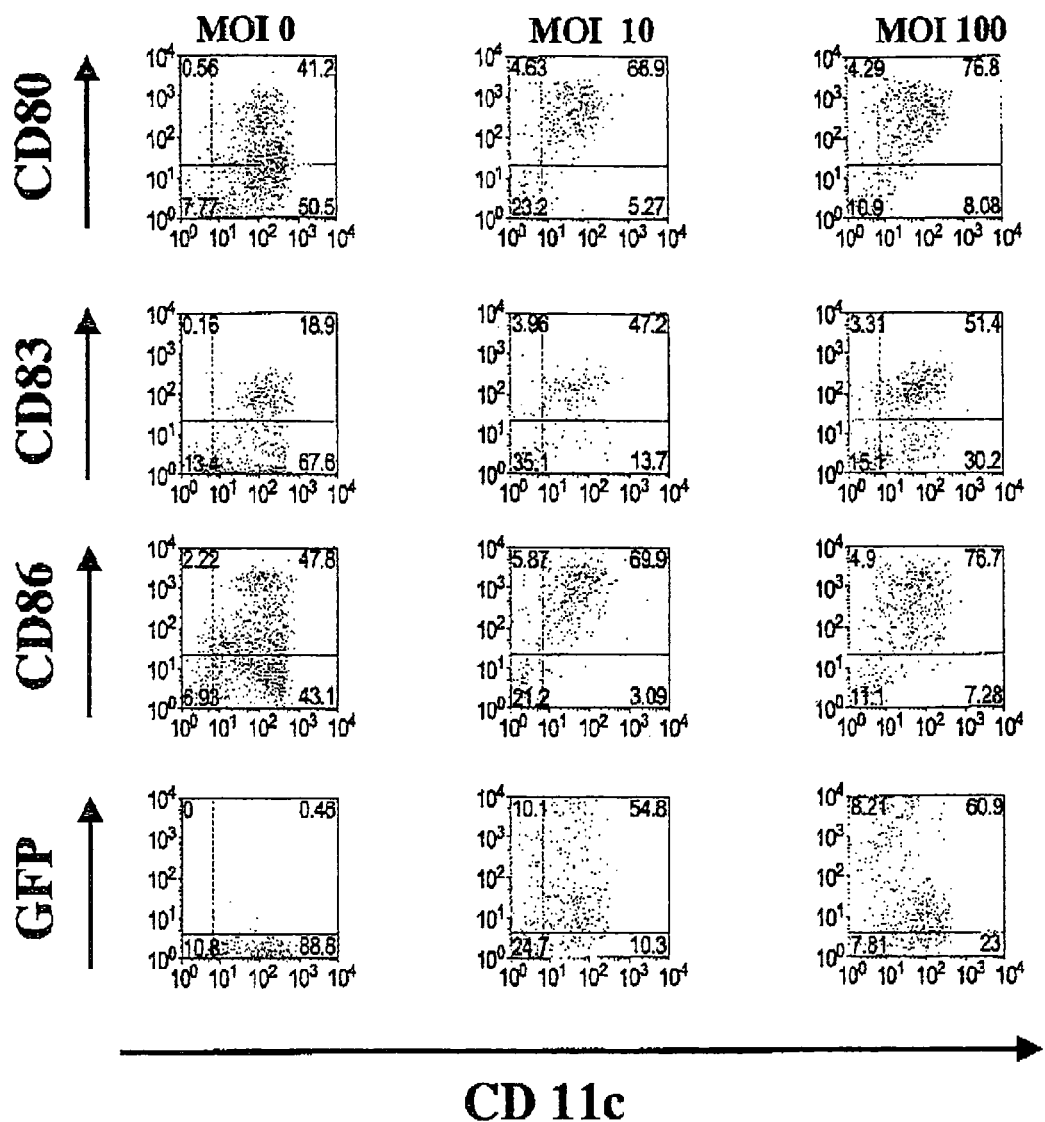
FIG. 12 depicts graphs showing gene transfer into DCs derived from cord blood.

Reports of other viral vectors described success in producing gene-transferred DCs through the introduction of genes into CD34 cells and the induction of differentiation into DCs Immunol. Meth. 2002; 153-165). A similar method was used for SeV-GFP. CD34 positive stem cells (CD34>90%) were separated from human cord blood using CD34 microbeads. After infection at an MOI of 0, 10, or 100 the cells were washed well. The cells were cultured in RPMI+10% FCS supplemented with SCF (50 ng/ml), GM-CSF (500 U/ml), and TNF-alpha (50 ng/ml) for three days, then passaged in a medium supplemented with SCF (50 ng/ml), GM-CSF (500 U/ml), IL-4 (250 U/ml), and TNF-alpha (50 ng/ml) (half of the medium was exchanged every three to four days), and GFP expression was examined 13 days after viral infection. As a result, gene transfer efficiency reached 65% to 70%, and DCs with a GFP expression efficiency better than those prepared with other vectors were prepared. By analyzing the expression of costimulatory molecules, more activated DCs were recovered from infected DCs than from uninfected DCs. (FIGS. 11 and 12).

The Examples described above demonstrated that the introduction efficiency of RNA viruses is considerably higher than that of lentiviruses or retroviruses, and an efficiency comparable to that of adenoviruses can be achieved rapidly and very easily. In addition, it was found that the activation markers did not change when using other vectors; however, it was shown that DC activation can be induced by infection with an RNA virus.

B. Evaluation of DC Function After Introduction

[Experiment 1]

DCs were infected with SeV-GFP at an MOI of 30 to 50. On the following day, the cells were stimulated by LPS (for two days), and then tested for the expression of costimulator molecules. As controls, the conditions of LPS stimulation only, SeV-GFP infection only, and neither LPS stimulation nor SeV-GFP infection were examined and compared.

Figure 13:
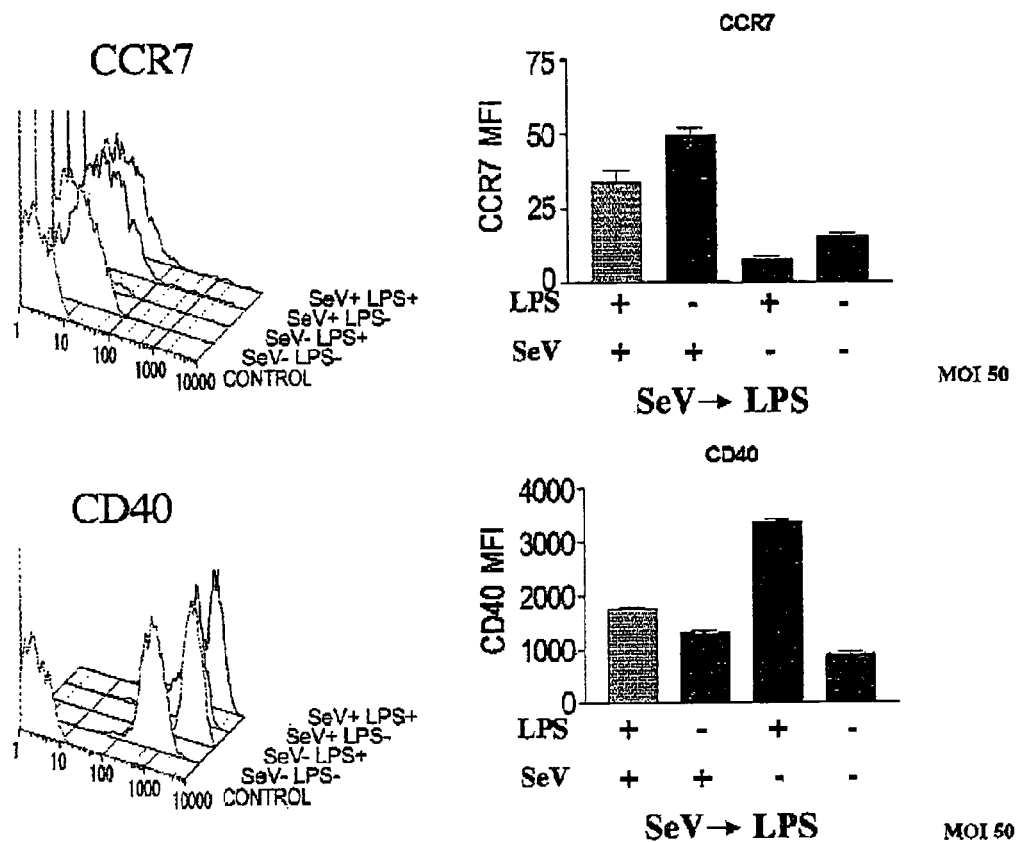
FIG. 13 depicts graphs showing the expression of costimulatory molecules after gene transfer (as compared with LPS stimulation).
Figure 14:
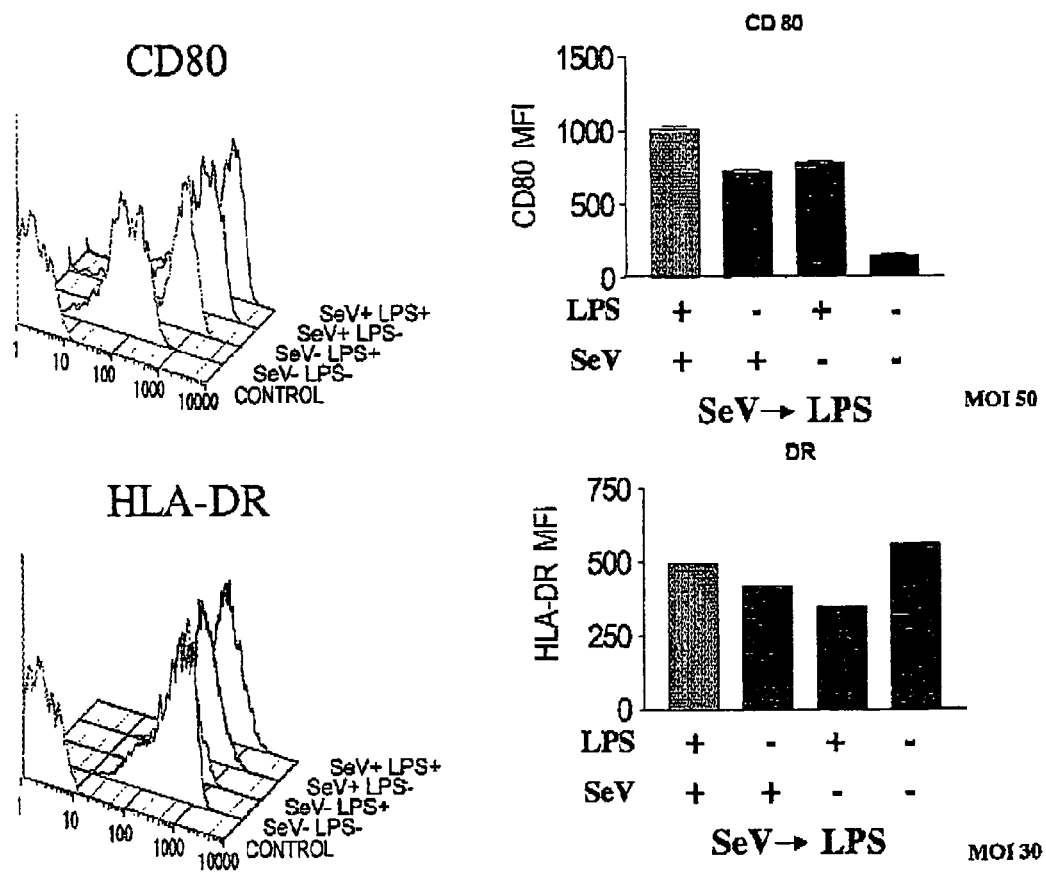
FIG. 14 depicts graphs showing the expression of costimulatory molecules after gene transfer (as compared with LPS stimulation).
Figure 15:
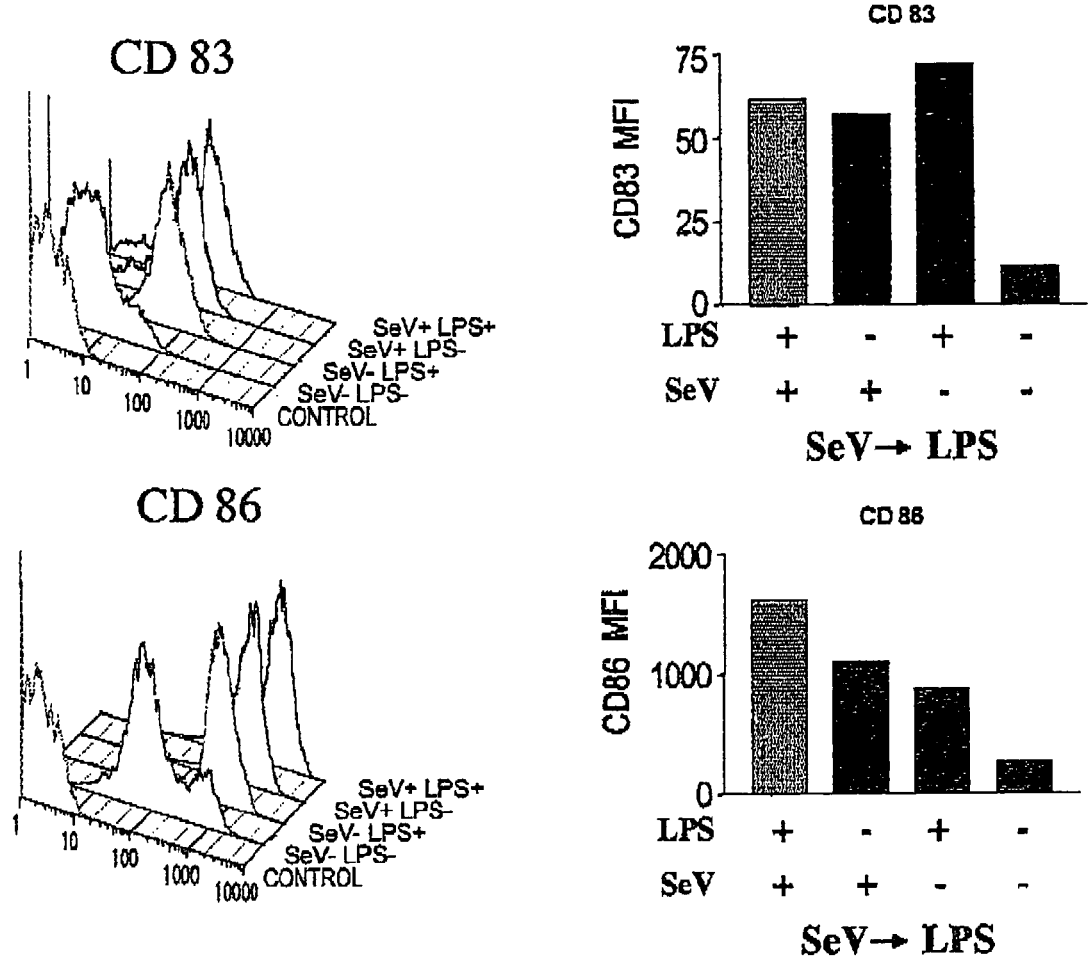
FIG. 15 depicts graphs showing the expression of costimulatory molecules after gene transfer (as compared with LPS stimulation).

Results: The obtained results demonstrate that DC activation occurs only upon SeV infection.
  Comparable to LPS: CD80(+) HLA-DR(−) CD83(−)
  Higher than LPS: CD86(+) CCR7(−)
  Lower than LPS: CD40(−)
(+) indicates where a synergistic effect can be obtained by using LPS and SeV. (FIGS. 13 to 15)

[Experiment 2]

DCs were infected with SeV-GFP at an MOI of 30 (some groups were stimulated with LPS on the day after infection or three days after infection). The phagocytic activity was examined in the groups in the same way as described in Experiment 1 (1 μm PCV-RED latex-microspheres were used; the bar graphs represent the activity after subtraction of positive background at 4° C.).

Figure 16:
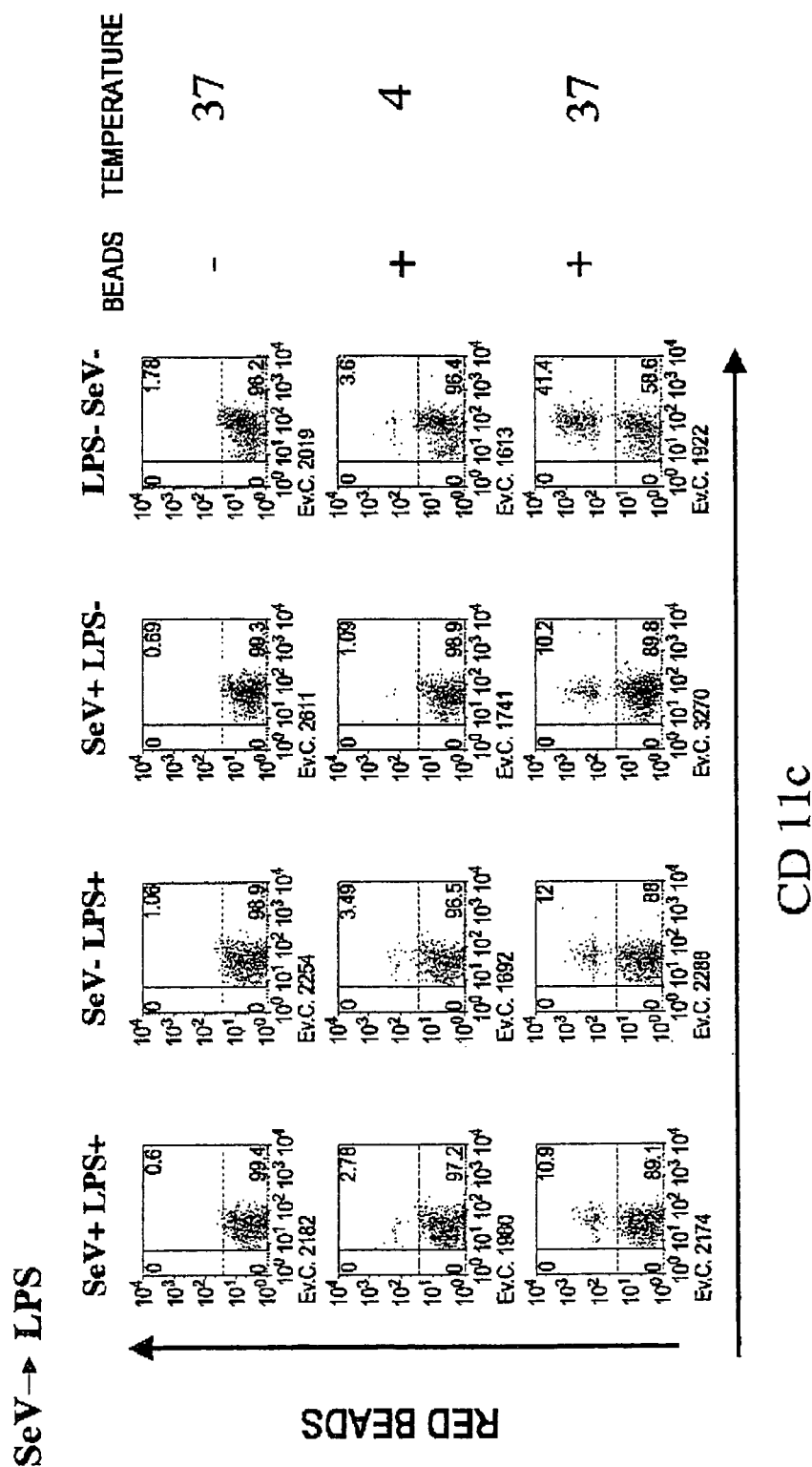
FIG. 16 depicts graphs showing phagocytic ability after gene transfer.
Figure 17:
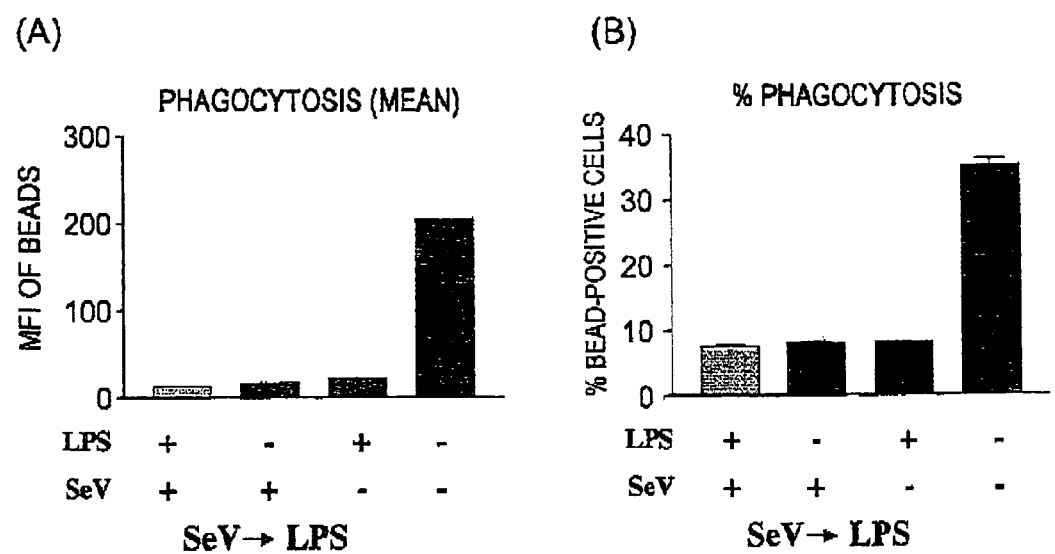
FIG. 17 depicts graphs showing phagocytic ability after gene transfer.

Results: Phagocytic activity was found to be reduced in cells infected with SeV due to the activation, as was also seen with the activation markers. In particular, the higher the GFP expression level, the lower the phagocytic activity. Thus, for example, when a tumor cell lysate is used to present tumor antigens on DCs, it is preferable to co-culture the DCs with the lysate before introducing the RNA virus to the DCs. (FIGS. 16 to 17).

[Experiment 3]

To examine the cytokine-producing ability of dendritic cells associated with the activation of the dendritic cells by RNA viruses monocyte-derived dendritic cells (MoDCs) obtained by seven days of culture were cultured in 12-well plates for 48 hours ($8 \times 10^5$/2 ml/wel medium supplemented with X-vivo15™, 2% autoserun, GM-CSF (500 UIml), and IL-4 (250 U/ml)) under the conditions described below. The levels of TNF-alpha, IL-1beta, IL-6, and IL-8 in the resulting supernatants were measured using Luminex™ system. SeV was infected at an MOI of 30 and the cells were cultured for two days.
  Unstimulated group: a group with medium only;
  Allantoic fluid group: a group to which was added 60 μl of hen egg allantoic fluid (free of SeV), which was a suspension of SeV;
  UV-SeV-GFP group: a group to which was added 60 μl of SeV-GFP solution whose replication ability is deprived by ultraviolet light irradiation; and
  SeV-GFP group: a group to which was added 60 μl of SeV-GFP solution (replication-competent SeV).

Figure 18:
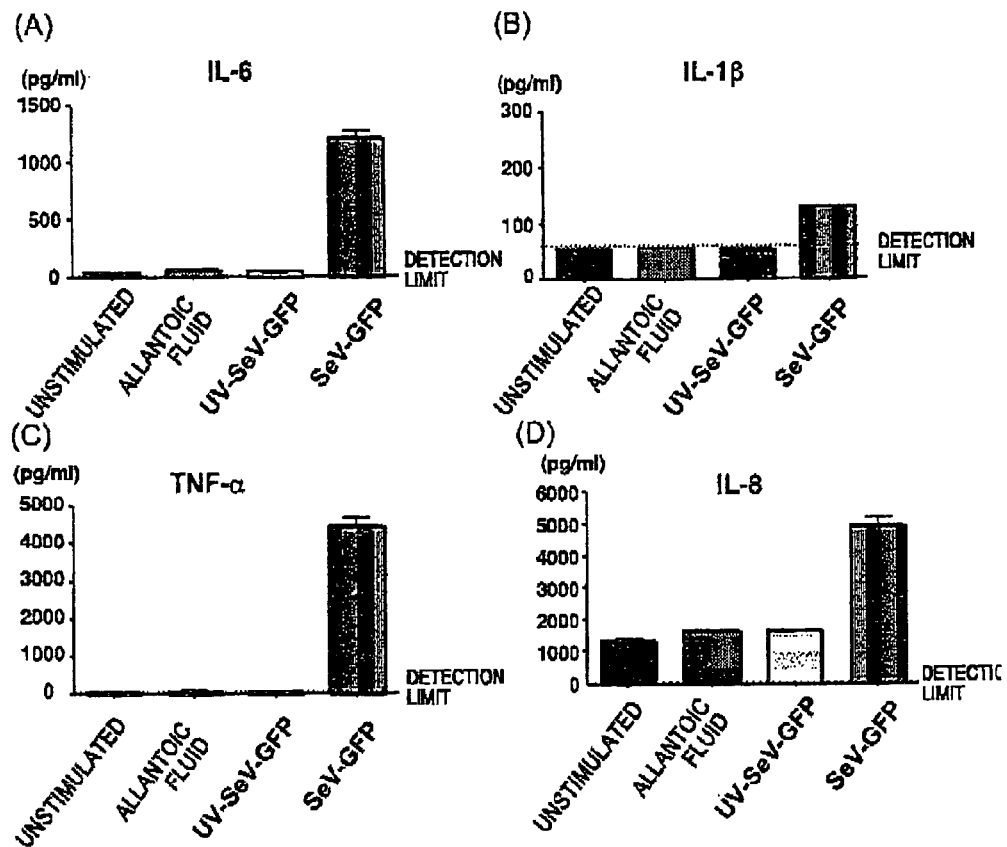
FIG. 18 depicts graphs showing cytokine production in monocyte-derived DCs after the introduction of an RNA virus.
Figure 19:
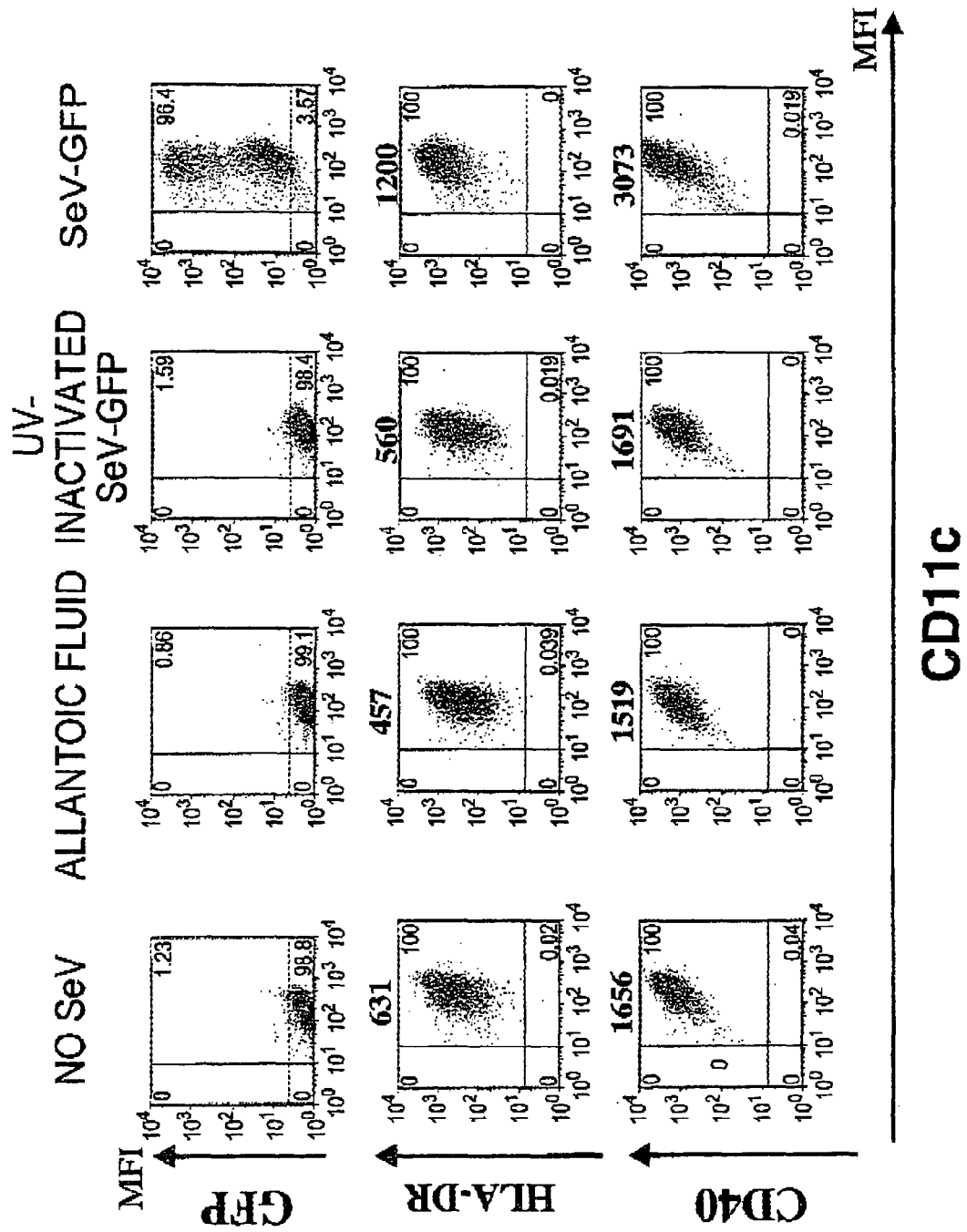
FIG. 19 depicts graphs showing the expression of marker proteins on the dendritic cells after introduction of an RNA virus.
Figure 20:
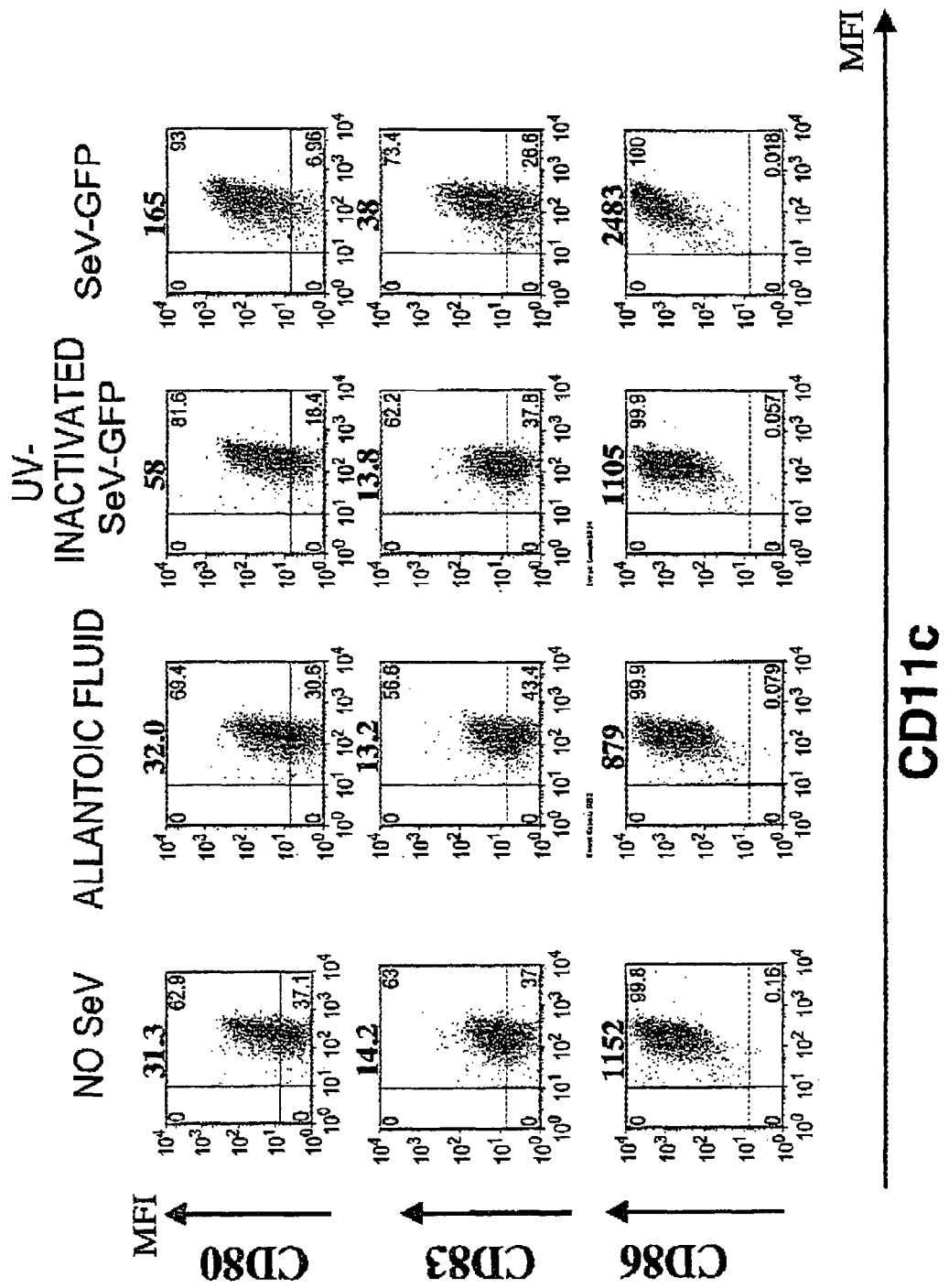
FIG. 20 depicts graphs showing the expression of marker proteins on the dendritic cells after introduction of an RNA virus.

Results: TNF-alpha, IL-1beta, and IL-6 was produced and the production of IL-8 was increased only in the dendritic cells introduced with GFP gene using replication-competent SeV without UV irradiation (FIG. 18). The increased expression levels of CD40, CD80, CD83, CD86, and HLA-DR in the dendritic cells were induced only by the replication-competent SeV (FIGS. 19 and 20). This means that the production of proinflammatory cytokines, which are important during the immune response, can be elicited in dendritic cells merely by introducing SeV into the dendritic cells. Further, since UV-treated SeV was not able to induce cytokine production, it was also suggested that it is not the contact of SeV with receptors on the membrane of dendritic cells at the time of gene transfer into the dendritic cells, but the process of viral genome RNA amplification after SeV infection that is critical to the activation of dendritic cells.

[Experiment 4]

To examine the antigen-presenting ability of dendritic cells associated with the activation of dendritic cells by RNA viruses, T cell activating ability was examined by irradiating the above DCs at 3000 rad, using the same experimental groups as above. (Purified (CD3+>95%) allo or syngenic T cells were cocultured with DCs at various DC doses for three days). Syngenic T cells were used as an indicator of response to SeV-GFP.

Figure 21:
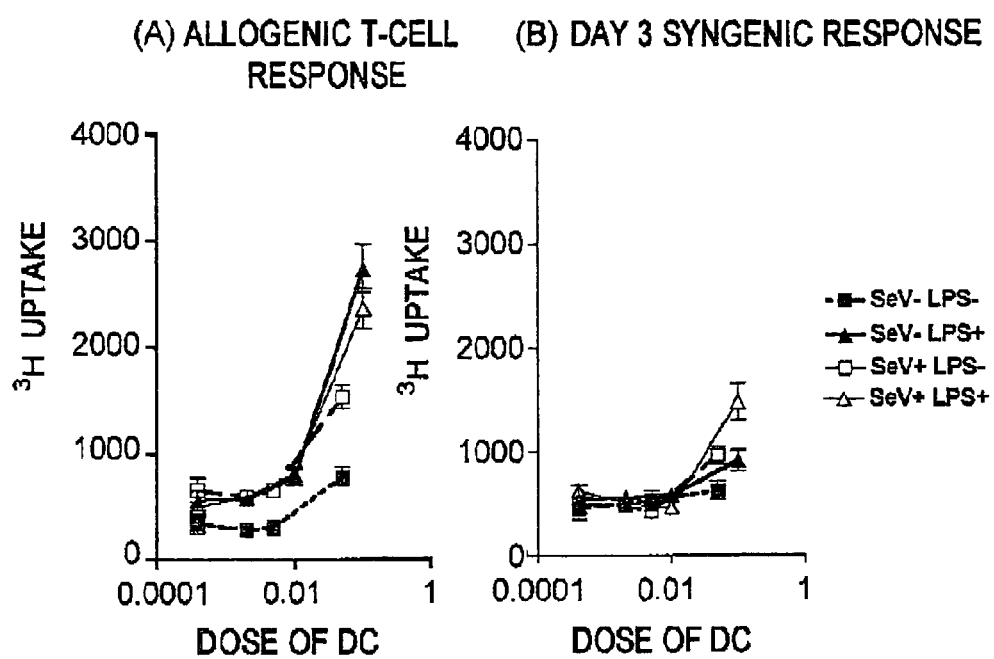
FIG. 21 depicts graphs showing the allo-T-cell stimulating ability of DCs introduced with an RNA virus.

Results: Due to the low DC ratio and low number of T cells, the differences were relatively insignificant; however, SeV infection alone was shown to have an allo T cell-stimulating effect equivalent to LPS (FIG. 21). DCs can also be used without irradiation.

[Experiment 5]

The antigen-presentation ability of dendritic cells after activation of dendritic cells by a RNA virus was compared with that conferred by stimulation with a cytokine cocktail, which has to date been thought to have the strongest effect on dendritic cell maturation. Human monocyte-derived dendritic cells (MoDC) that had been obtained by seven days of culture were cultured in 12-well plates for 48 hours [$1 \times 10^6$ cells/2 ml/well: the medium used was X-vivo15™ supplemented with 2% autoserum, GM-CSF (500 U/ml), and IL-4 (250 U/ml); the culture conditions are described below for each group]. An F gene-lacking Sendai virus carrying temperature-sensitive mutant M and HN protein genes (M gene: G69E, T116A, and A183S; HN gene: A262T, G264R, and K461G), and mutant P and L protein genes for persistent infection (P gene: L511F; L gene: N1197S and K1795E) (SeV-dFM$^{ts}$HN$^{ts}$PLmut-GFP (also abbreviated as SeV/TS dF)) was also used as an RNA virus for comparison (WO 2003/025570; Inoue M, et al. J Virol 2003; 77:3238-3246; Inoue M, et al. Mol. Ther. 2003; 7(5):S37). This virus had lost the ability to form infectious virions in infected cells.
  SeV(−) group: group treated with medium alone
  SeV-dFM$^{ts}$HN$^{ts}$PLmut-GFP group: group treated with SeV-dFM$^{ts}$HN$^{ts}$PLmut-GFP (F gene-lacking M/HN/P/L mutant SeV carrying GFP) at an MOI of 50
  SeV-GFP group: group treated with SeV-GFP (Transmissible SeV carrying GFP) solution at a MOI of 50
  Cytokine cocktail group: group treated with cytokine cocktail (50 ng/m IL-1β, 500 ng/ml IL-6, 2500 U/ml INF-α, 100 ng/ml TNF-α, and 20 μM PGE$_2$)

Figure 22:
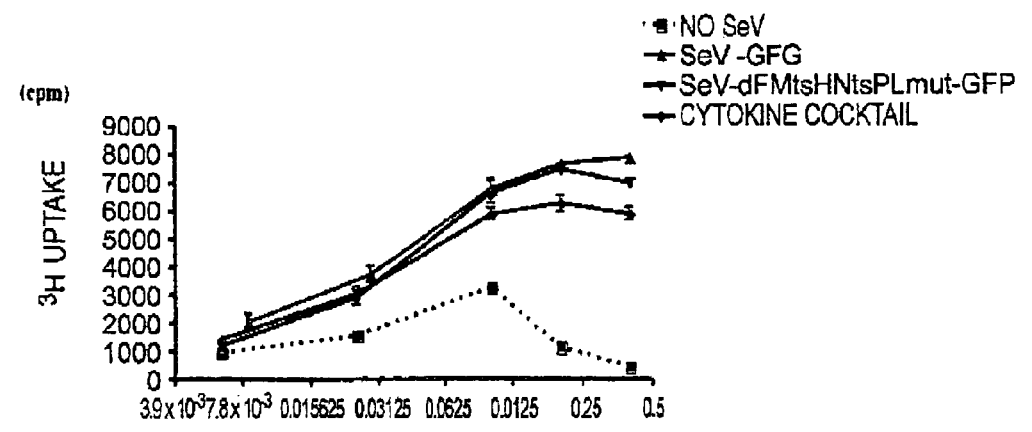

MoDC after 48 hours were irradiated at a dose of 30 Gy. Then the MoDC ($4 \times 10^4$ to $6.25 \times 10^2$ cells/well) and peripheral blood-derived allogenic T cells ($1 \times 10^5$ cells/well) [96% or more pure T cells obtained from allogenic peripheral blood by using RosetteSep™-human T cell enrichment kit (Stem-Cell Technologies, Vancouver, Canada)] were cultured for four days. 1 μCi of [$^3$H]-thymidine was added to each well, and after eight hours the incorporated [$^3$H]-thymidine was counted using Beta Plate System (Pharmacia LKB Biotechnology, Uppsala, Sweden). The medium used was X-vivo15™ supplemented with 2% autoseruin. The X axis in the Figure shown indicates the [number of cultured MoDC per well/number of T cells per well ($=1 \times 10^5$ cells)], and the Y axis indicates the amount of [$^3$H]-thymidine incorporated (cpm (FIG. 22).

Results: Compared with non-stimulated dendritic cells, dendritic cells infected with SeV-GFP allowed significant growth of allogenic T cells. The ability was found to be comparable to or stronger than that of the cytokine cocktail stimulation, which has to date been thought to have the strongest ability of dendritic cell maturation. Dendritic cells infected with F-deficient HN temperature-sensitive SeV (SeV-dFM$^{ts}$HN$^{ts}$PLmut-GFP) were also found to have almost comparable antigen-presenting ability (FIG. 22).

C. Induction of Cancer Antigen-Specific CTLs

Using the method described above in subsection A, CD14+ cells were enriched from human peripheral blood (healthy donors with HLA-A 0201), and immature dendritic cells were prepared using x-vivo 15™ (Cambrex)+2% autoserum as a medium, supplemented with GM-CSF (500 U/ml), and IL-4 (250 U/ml) (half of the medium was exchanged every three to four days). The prepared immature dendritic cells were divided into the following three group and then firer cultured for 48 hours in the presence of GM-CSF (500 U/ml) and IL-4 (250 U/ml):

Group 1: no addition;
Group 2: infected with SeV-GFP (MOI 30); and
Group 3: stimulation by cytokine cocktail (50 ng/ml IL-1β, 500 ng/ml IL-6, 2500 U/ml IFN-α, 100 ng/ml TNF-α, and 20 µM PGE2).

Next, dendritic cells were recovered and pulsed with MART-1 peptide (EAAGIGILTV (SEQ ID NO: 1); 50 pg/ml for three hours). T cells in peripheral blood from the same healthy donor from whom the dendritic cells had been obtained were enriched through negative selection (CD3+ >97%), and were cultured with peptide-pulsed dendritic cells of the above three groups for seven days (X-vivo 15™+2% autologous serum). (Half of the medium was exchanged every three to four days or when the medium changed yellow. The T cells and dendritic cells were co-cultured in the absence of IL-2 for the first stimulation, and 100 U/ml IL-2 was added from the third day.) This treatment was repeated twice. The cells were recovered from each mixed culture fluid and used as effector cells in CTL assays.

T2 cells (TAP deficient cell line, a T cell-B cell hybridoma, obtained from a donor with HLA-A2+) were used as target cells. Since these cells lack TAP (the transporter to class I), the are incapable of leading peptides produced through cytoplasmic proteolysis to Class I. Thus, when a peptide is exogenously added, that peptide is loaded onto Class I, resulting in Class I expression. The target cells were pulsed with mutant MART-1 peptide (ELAGIGILTV (SEQ ID NO: 2))(this is a peptide with potentiated HLA-A2 binding ability without any alterations in the T cell receptor recognition site, as compared to the peptide used in the above-described stimulation) or with influenza peptide (Flu; a peptide as a third party; GILGFVFTL (SEQ ID NO: 3)), and labeled with Cr. The effector T cells of the above three groups were co-cultured with each of the two types of targets at a ratio of 20:1, 10:1, 5:1, or 2.5:1 for four hours to examine the CTL activity.

The combinations used in the experiment are summarized below.

| Effector cells | Target cells | Symbols in the figure |
| --- | --- | --- |
| Effector T cells of Group 1 | Mutant MART1 peptide + T2 cells | Solid line with closed squares |
| Effector T cells of Group 2 | Mutant MART1 peptide + T2 cells | Solid line with closed triangles |
| Effector T cells of Group 3 | Mutant MART1 peptide + T2 cells | Solid line with closed inverted triangles |
| Effector T cells of Group 1 | Flu peptide + T2 cells | Dotted line with closed diamonds |
| Effector T cells of Group 2 | Flu peptide + T2 cells | Dotted line with closed circles |
| Effector T cells of Group 3 | Flu peptide + T2 cells | Dotted line with open squares |

Figure 23:
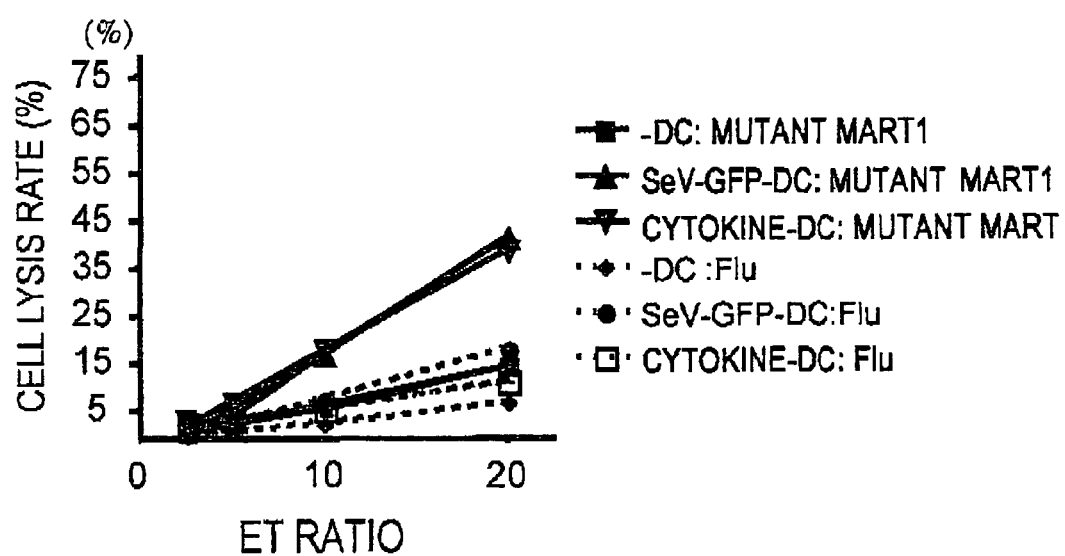
FIG. 23 depicts the results of in vitro induction of MART-1-specific CTLs by introducing an RNA virus.

Results: MART-1 specific CTL cannot be induced when the T-cells are stimulated by the non-activated DCs (MART1 peptide+) in the three groups described above; however, as a positive control, when T cells were stimulated using dendritic cells activated by cytokines (the method which most intensively activates cells from among the current dendritic cell therapies for anti-tumor immunity), MART-1 specific CTLs could be induced (a similar result was obtained when the MART-1 peptide used in the stimulation was used instead of the mutant MART-1 peptide to pulse the target). When dendritic cells introduced with SeV were used, CTL activity comparable to the positive control was obtained (FIG. 23). Thus, CTL assays demonstrated the dendritic cells were activated by SeV infection alone, and that they can induce CTLs in vitro to the same level as dendritic cells activated by cytokines. When SeV is used to activate T cells, the activation can be achieved at the same time as the target gene is introduced, making the addition of activation factors such as cytokines unnecessary, and thus contributing to reduced costs, time savings, and retained cell viability.

D. Cancer Growth Suppression by DCs Introduced with RNA Viruses

These Examples outline examples of the methods for treating tumors by in vivo and ex vivo administration of RNA viruses.

(Experiment 1)

The tumor model used was a B16 melanoma-transplanted model that expresses MHC class I at very low levels and has poor immunogenicity. C57BL/6 mice (six to eight weeks old female) (Charles River Japan, Inc.) were used as the tumor model mice, and dendritic cells were collected from C57BL/6 mice (eight weeks old; female) (Charles River Japan, Inc.). The dendritic cells were obtained by collecting bone marrow from the thigh bones of C7BL/6 mice removing T cells using SpinSep™, murine hematopoietic progenitor enrichment cocktail (anti-CD5 antibody, anti-CD45R antibody, anti-CD11b antibody, anti-Cr-1 antibody, anti-TER119 antibody, anti-7/4 antibody; Stem Cell technology); and then culturing the cells for one week with the addition of IL-4 and GM-CSF. On day 0, $1 \times 10^5$/100 µL of B16 melanoma cells were subcutaneously (s.c.) inoculated into the abdominal area of the mice. On days 10, 11 and 24, dendritic cells not stimulated for activation, dendritic cells activated with LPS (LPS DC or dendritic cells activated by introducing SeV-GFP or SeV-IFNβ expressing mouse interferon (SeV GFP DC and SeV IFNβ DC, respectively) were administered to the area surrounding the tumor. At this time another experiment was also carried out, wherein the dendritic cells were administered after pulsing with tumor antigens (tumor lysate obtained by freeze and thaw of B16). In addition to these experiments, another experiment was also conducted, whereby ten days after tumor injection (day 10) SeV-IFNβ was directly injected intratumorally to examine it anti-tumor effect.

SeV was introduced into dendritic cells by infecting dendritic cells cultured for one week as described above with SeV-IFNβ at an MOI of 40, and then culturing the cells for eight hours. When the dendritic cells were pulsed with tumor antigens, dendritic cells cultured for one week as described above were recovered and pulsed using tumor lysate as the tumor antigen (DC:tumor lysate=1:3), then cultured for 18 hours, infected with SeV-IFNβ at an MOI of 40, and cultured for eight hours. These dendritic cells were then recovered and $5 \times 10^5$ to $10 \times 10^5$ cells were administered to the area surrounding the mice tumors.

Figure 24:
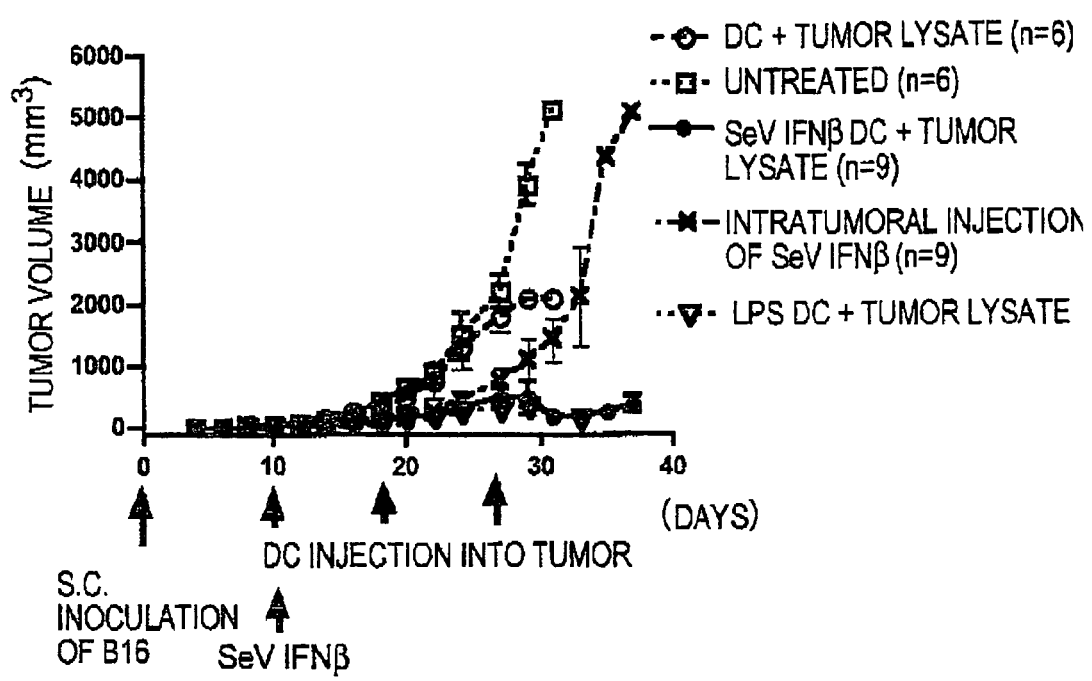
FIG. 24 depicts the growth curve for subcutaneously inoculated B16 melanoma cells.

As shown in FIG. 24, both direct intratumoral injection of SeV-INFβ and its ex vivo administration via dendritic cells suppressed tumor growth. In particular, a very strong tumor-suppressing effect was observed in mice treated with DC/SeV-IFNβ.

The anti-tumor effect in each of the therapeutic groups described above was more closely examined. To assay natural killer (NK) cell activity, spleens were excised from mice in each of the above therapeutic groups seven days after the end of three rounds of DC therapy, and effector cells were prepared. A $^{51}$Cr release assay was performed using Yac-1 as the target. Further, to assay the cytotoxicity of T lymphocytes, the spleen cells remaining from the NK cell activity assay described above were cultured for five days with TRP-2 peptide, a B16 tumor antigen, for use as effector cells. These effector cells were co-cultured with EL-4 target cells pulsed with mTRP-2 peptide, and then a $^{51}$Cr release assay was performed. The rate of specific $^{51}$Cr release was calculated as follows:

[(sample (cpm)−spontaneous emission (cpm))/(maximum emission (cpm)−spontaneous emission (cpm))]×100 where the maximum emission was determined using target cells incubated with 1% triton X, and spontaneous emission was determined using target cells incubated with culture medium alone.

Figure 25:
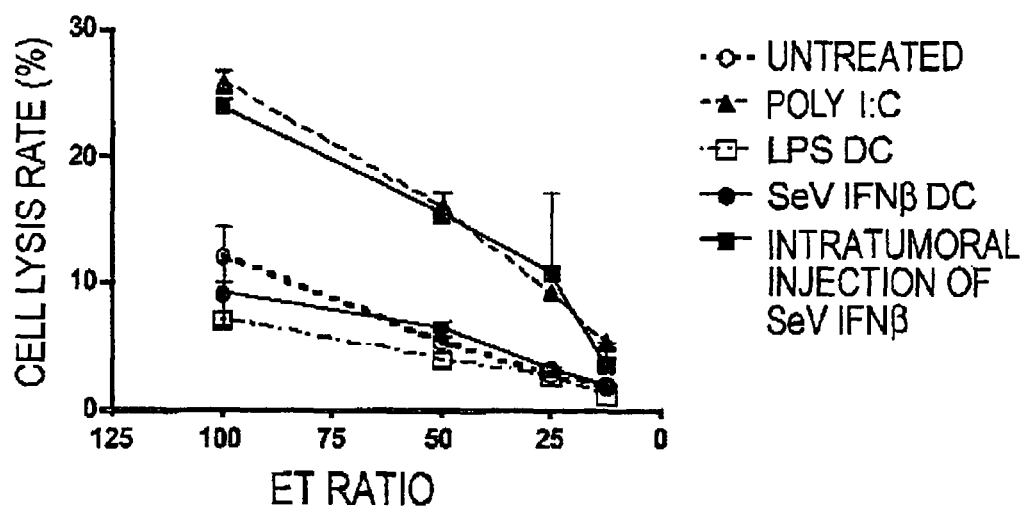
FIG. 25 depicts the results of a 51Cr release assay for YAC-1 target cells.
Figure 26:
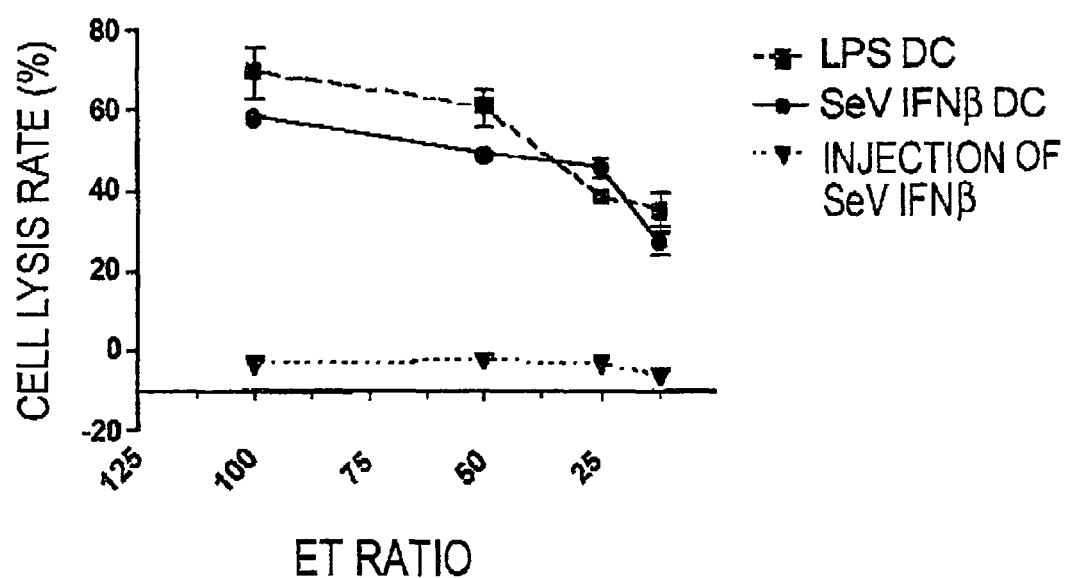
FIG. 26 depicts the results of a 51Cr release assay for TRP2 peptide+EL-4.

The activation of natural killer (NK) cells was only detected in mice that were directly injected with SeV, and not in the group administered with dendritic cells (FIG. 25). In contrast, the activation of cytotoxic T lymphocytes (CTLs) was most strong in the DC/LPS treated group and in mice treated with DC/SeV-IFNβ, slightly lower in the DC/SeV-GFP treated group, and was not detected in the group directly injected with Se-IFNβ (FIG. 26). The tumor lysate pulsing had no significant influence on tumor growth, nor on CTL response. Thus, it was demonstrated that strong anti-tumor therapeutic effects were exerted by tumor immunotherapy using dendritic cells introduced with immunostimulatory cytokine genes using SeV. Despite the slight difference in CTL activity between the DC/LPS-treated group and the DC/SeV-IFNβ-treated group, their anti-tumor effects were found to be comparable. Thus, while direct administration of SeV-IFNβ strongly activated NK cells, indirect administration via dendritic cells was revealed to induce CTL activity. Therefore, treatments combining these art expected to be more effective.

[Experiment 2]

Figure 27:
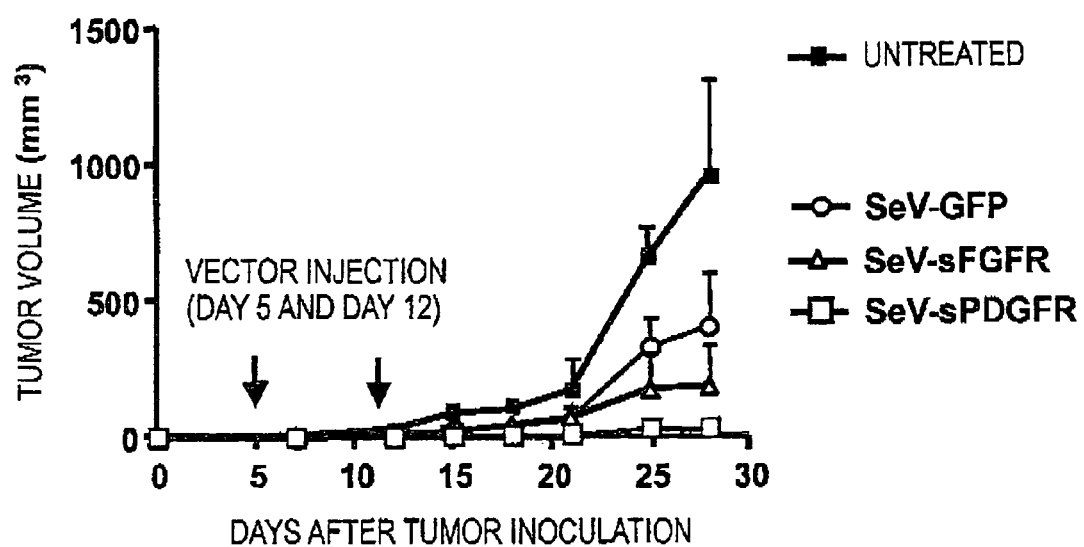
FIG. 27 depicts a graph showing the therapeutic effect on melanomas when an SeV expressing GFP, an SeV expressing soluble FGF receptor, or an SeV expressing soluble PDGFRα was administered in vivo.

C57BL/6 mice (six to eight weeks old, female) were inoculated subcutaneously in the ventral area with 1×10$^5$ cells of melanoma cell line B16F1 (ATCC CRL-6323)(n=4). Five (day 5) and 12 days (day 12) after inoculation, SeV crying no special therapeutic gene (SeV expressing GFP; SeV-GFP), Sendai virus expressing soluble human FGF receptor (SeV-sFGFR or Sendai virus expressing soluble human PDGFRα (SeV-hsPDGFRα) was injected into tumors at a dose of 1×10$^8$ U PFU, and tumor size was then measured over time. The results showed the tumor size was significantly reduced in all the SeV-administered groups as compared with the SeV non-administered group (FIG. 27). As described above, an antitumor effect was exerted upon in vivo administration of SeV, even when the SeV used was not carrying a therapeutic gene The tumor growth-suppressing effect produced upon administering the SeV expressing soluble FGF receptor was found to be stronger than that for the group administered with SeV-GFP. The antitumor effect was strongest, and tumor size hardly increased, when the SeV expressing soluble PDGFRα was administered.

[Experiment 3]

C57BL/6 mice (six weeks old; female) were inoculated subcutaneously in the ventral area with 1×10$^5$ cells of melanoma cell line B16F1 (ATCC CRL-6323) (n=4). Independently, marrow cells were collected from C57BL/6 mice (six to eight weeks old, female), and cells obtained by negative selection using SpinSep™ (Stem Cell Technologies Inc.) based on CD45R CD5, CD11b, TER119, GT-1, and 7-4-were cultured for seven days in the presence of 250 IU/ml GM-CSF and 250 IU/ml IL-4. Mouse marrow cell-derived dendritic cells were thus prepared. For gene introduction, the dendritic cells were infected with Sendai virus carrying no therapeutic gene (SeV expressing GFP; SeV-GFP) at an MOI of 60, or with Sendai virus expressing soluble human PDGFα receptor (SeV-hsPDGFRα), Sendai virus expressing tumor antigen TRP2 (SeV-TRP2), or Sendai virus expressing tumor antigen gp100 (SeV-gp100) at an MOI of 20.

Figure 28:
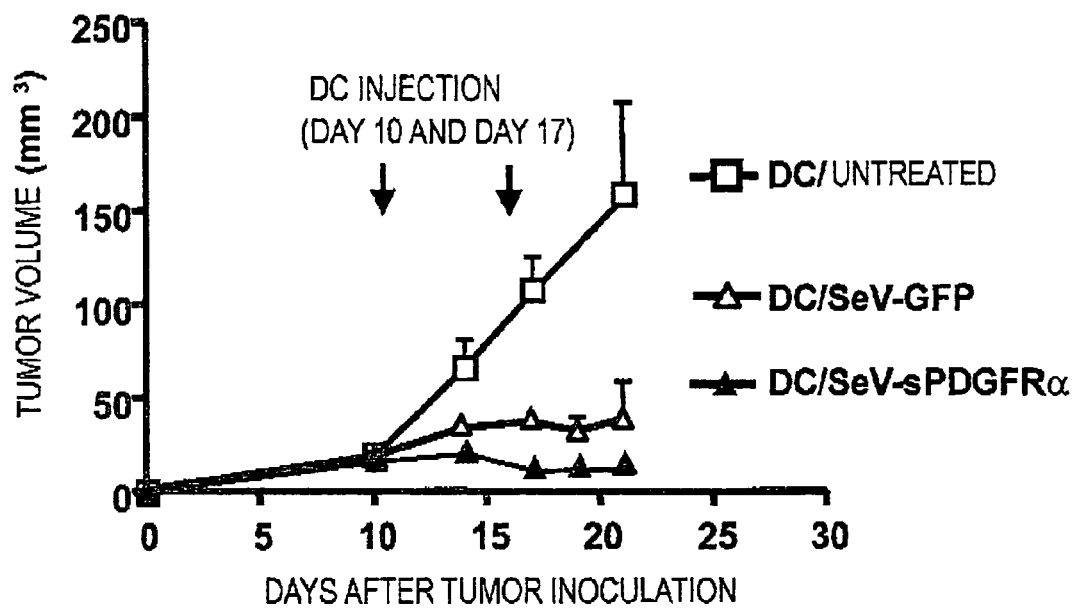
FIG. 28 depicts a graph showing the therapeutic effect on melanomas when dendritic cells introduced with an SeV expressing GFP or an SeV expressing soluble PDGFRα were administered ex vivo.

1×10$^6$ dendritic cells introduced with SeV-GFP or SeV-hsPDGFRα were injected into tumors ten (day 10) and 17 days (day 17) after inoculation with B16F1. Tumor size was then measured over time. The results are shown in FIG. 28. Like the results of the above-describe in vivo administration of the viruses, tumor size was also significantly reduced in mice administered with dendritic cells car SeV-GFP as compared with mice administered with dendritic cells carrying no SeV. The ex vivo administration of SeV using dendritic cells produced a more marked antitumor effect than the in vivo administration of SeV (FIG. 28). When dendritic cells carding SeV expressing soluble PDGFRα were administered ex vivo, the antitumor effect became stronger and tumor size hardly increased.

INDUSTRIAL APPLICABILITY

The present invention provided anticancer agents comprising as active ingredients dendritic cells introduced with RNA viruses. The introduction of an RNA virus induces the activation of dendritic cells, and thus the step of activation by treatment with cytokines and such after introduction can be omitted. The present invention is thus expected to contribute to sustained cell viability, reduced costs, and further reductions in the time required for ex vivo procedures. The present invention allows novel virotherapy using RNA viruses and dendritic cells in combination.

The invention claimed is:

1. A method for producing an anticancer agent, which comprises:

introducing a Sendai virus Z strain able to replicate its genome into a CD11c+immature dendritic cell, wherein said genome of the Sendai virus undergoes replication in the dendritic cell, thereby inducing maturation of said dendritic cell, and formulating the anticancer agent comprising the dendritic cell containing the virus and a pharmaceutical acceptable carrier or media.

2. A method for suppressing a cancer, which comprises:

introducing a Sendai virus Z strain able to replicate its genome into a CD11c+ immature dendritic cell, wherein said genome of the Sendai virus undergoes replication in the dendritic cell, thereby inducing maturation of said dendritic cell, and administering to a subject having a cancer the dendritic cell containing the virus able to replicate its genome.

3. The method claim 1, wherein the virus does not contain a foreign gene.

4. The method claim 2, wherein the virus does not contain a foreign gene.

5. The method of claim 1, wherein the virus does not form an infectious virion.

6. The method of claim 2, wherein the virus does not form an infectious virion.

7. The method of claim 1, wherein the virus encodes an IFN-β.

8. The method of claim 2, wherein the virus encodes an IFN-β.

9. The method of claim 1, wherein the virus encodes a soluble FGF receptor.

10. The method of claim 2, wherein the virus encodes a soluble FGF receptor.

11. The method of claim 1, wherein the virus encodes a soluble PDGF receptor α.

12. The method of claim 2, wherein the virus encodes a soluble PDGF receptor α.

13. The method of claim 2, wherein the virus is an infectious or non-infectious virion.

14. The method of claim 2, wherein the virus is an infectious or non-infectious virion.

15. The method of claim 1, wherein the virus is a genome RNA-protein complex.

16. The method of claim 2, wherein the virus is a genome RNA-protein complex.

17. The method claim 1, wherein said virus is SeV-GFP or an attenuated or temperature-sensitive mutant thereof, wherein said Sendai virus has further been modified not to contain a foreign gene or modified to encode a desired foreign gene.

18. The method claim 2, wherein said virus is SeV-GFP or an attenuated or temperature-sensitive mutant thereof, wherein said Sendai virus has further been modified not to contain a foreign gene or modified to encode a desired foreign gene.

* * * * *

UNITED STATES PATENT AND TRADEMARK OFFICE
CERTIFICATE OF CORRECTION

Page 1 of 1

PATENT NO.       : 8,889,118 B2
APPLICATION NO.  : 11/630532
DATED            : November 18, 2014
INVENTOR(S)      : Shinji Okano et al.

It is certified that error appears in the above-identified patent and that said Letters Patent is hereby corrected as shown below:

In the Claims,

Column 32, Line 35, in Claim 13, replace "The method of claim 2," with --The method of claim 1,--.

Signed and Sealed this
Fifth Day of May, 2015

Michelle K. Lee
*Director of the United States Patent and Trademark Office*